(12) United States Patent
Velis

(10) Patent No.: US 11,446,178 B2
(45) Date of Patent: Sep. 20, 2022

(54) COLD SLURRY CONTAINMENT

(71) Applicant: MIRAKI INNOVATION THINK TANK LLC, Cambridge, MA (US)

(72) Inventor: Christopher Velis, Cambridge, MA (US)

(73) Assignee: MIRAKI INNOVATION THINK TANK LLC, Cambridge, MA (US)

(*) Notice: Subject to any disclaimer, the term of this patent is extended or adjusted under 35 U.S.C. 154(b) by 1054 days.

(21) Appl. No.: 15/946,474

(22) Filed: Apr. 5, 2018

(65) Prior Publication Data

US 2018/0289538 A1 Oct. 11, 2018

Related U.S. Application Data

(60) Provisional application No. 62/482,008, filed on Apr. 5, 2017.

(51) Int. Cl.
*A61F 7/12* (2006.01)
*A61M 25/10* (2013.01)
(Continued)

(52) U.S. Cl.
CPC ............ *A61F 7/123* (2013.01); *A61F 7/12* (2013.01); *A61M 25/007* (2013.01); *A61M 25/1002* (2013.01); *A61B 2090/0463* (2016.02); *A61F 2007/0056* (2013.01); *A61F 2007/0063* (2013.01); *A61F 2007/0069* (2013.01);
(Continued)

(58) Field of Classification Search
CPC ............ A61B 2090/0463; A61B 90/00; A61F 2007/0056; A61F 2007/0063; A61F 2007/0069; A61F 2007/0092; A61F 2007/0096; A61F 2007/0249; A61F 2007/025; A61F 2007/0253; A61F 2007/126; A61F 7/12; A61F 7/123;
(Continued)

(56) References Cited

U.S. PATENT DOCUMENTS 3,373,906 A 3/1968 Hart et al.
3,893,834 A 7/1975 Armstrong
(Continued)

FOREIGN PATENT DOCUMENTS

CN 102271741 12/2011
CN 102307545 1/2012
(Continued)

OTHER PUBLICATIONS

Office Action dated Mar. 1, 2021 in Chinese Application No. 2017800786800, with English translation.
(Continued)

*Primary Examiner* — Tigist S Demie
(74) *Attorney, Agent, or Firm* — Wenderoth, Lind & Ponack, LLP

(57) ABSTRACT

The present invention provides methods and devices for controlling a cold slurry that is delivered to a target tissue and for limiting heat transferring from surrounding tissue to the target tissue. In particular, a balloon structure is deployed at or near a point of delivery to act as a physical and/or thermal barrier. In some instances, the balloon structure can act as a pressure device obstructing the flow of warm blood into a treatment area, which can melt the cold slurry.

19 Claims, 17 Drawing Sheets

(51) Int. Cl.
*A61M 25/00* (2006.01)
*A61F 7/00* (2006.01)
*A61F 7/02* (2006.01)
*A61B 90/00* (2016.01)

(52) U.S. Cl.
CPC ............... *A61F 2007/0092* (2013.01); *A61F 2007/0096* (2013.01); *A61F 2007/025* (2013.01); *A61F 2007/0249* (2013.01); *A61F 2007/0253* (2013.01); *A61F 2007/126* (2013.01); *A61M 2025/1013* (2013.01); *A61M 2025/1072* (2013.01)

(58) Field of Classification Search
CPC .. A61M 2025/1013; A61M 2025/1072; A61M 25/007; A61M 25/1002
See application file for complete search history.

(56) References Cited

U.S. PATENT DOCUMENTS

| | | | |
|---|---|---|---|
| 4,363,329 A | 12/1982 | Raitto | |
| 4,619,678 A | 10/1986 | Rubin | |
| 4,966,601 A | 10/1990 | Draenert | |
| 4,983,045 A | 1/1991 | Taniguchi | |
| 4,986,079 A | 1/1991 | Koseki et al. | |
| 5,143,063 A | 9/1992 | Fellner | |
| 5,304,128 A | 4/1994 | Haber et al. | |
| 5,445,523 A | 8/1995 | Fischer et al. | |
| 5,507,790 A | 4/1996 | Weiss | |
| 5,769,879 A | 6/1998 | Richards et al. | |
| 6,032,675 A | 3/2000 | Rubinsky | |
| 6,041,787 A | 3/2000 | Rubinsky | |
| 6,067,803 A | 5/2000 | Wolsey et al. | |
| 6,244,052 B1 | 6/2001 | Kasza | |
| 6,300,130 B1 | 10/2001 | Toner et al. | |
| 6,324,863 B1 | 12/2001 | Henry | |
| 6,334,328 B1 | 1/2002 | Brill | |
| 6,403,376 B1 | 6/2002 | Toner et al. | |
| 6,413,444 B1 | 7/2002 | Kasza | |
| 6,428,563 B1 | 8/2002 | Keller | |
| 6,430,957 B1 | 8/2002 | Inada et al. | |
| 6,458,109 B1 | 10/2002 | Henley et al. | |
| 6,475,212 B2 | 11/2002 | Dobak, III et al. | |
| 6,547,811 B1 | 4/2003 | Becker et al. | |
| 6,575,930 B1 | 6/2003 | Trombley, III et al. | |
| 6,673,607 B2 | 1/2004 | Toner et al. | |
| 6,849,072 B2 | 2/2005 | Lee et al. | |
| 6,962,601 B2 | 11/2005 | Becker et al. | |
| 7,118,591 B2 | 10/2006 | Frank et al. | |
| 7,276,051 B1 | 10/2007 | Henley et al. | |
| 7,367,341 B2 | 5/2008 | Anderson et al. | |
| 7,389,653 B2 | 6/2008 | Kasza et al. | |
| 7,422,601 B2 | 9/2008 | Becker et al. | |
| 7,507,234 B2 | 3/2009 | Utley et al. | |
| 7,588,547 B2 | 9/2009 | Deem et al. | |
| 7,603,868 B2 | 10/2009 | Sveinsson | |
| 7,681,411 B2 | 3/2010 | DiLorenzo | |
| 7,713,266 B2 | 5/2010 | Elkins et al. | |
| 7,854,754 B2 | 12/2010 | Ting et al. | |
| 8,117,854 B2 | 2/2012 | Lampe et al. | |
| 8,192,474 B2 | 6/2012 | Levinson | |
| 8,275,442 B2 | 9/2012 | Allison | |
| 8,285,390 B2 | 10/2012 | Levinson et al. | |
| 8,298,216 B2 | 10/2012 | Burger et al. | |
| 8,308,681 B2 | 11/2012 | Slocum et al. | |
| 8,337,539 B2 | 12/2012 | Ting et al. | |
| 8,505,315 B2 | 8/2013 | Kasza et al. | |
| 8,523,927 B2 | 9/2013 | Levinson et al. | |
| 8,535,275 B2 | 9/2013 | Salzman | |
| 8,603,073 B2 | 12/2013 | Allison | |
| 8,608,696 B1 | 12/2013 | DiMeo et al. | |
| 8,676,338 B2 | 3/2014 | Levinson | |
| 8,702,774 B2 | 4/2014 | Baker et al. | |
| 8,808,241 B2 | 8/2014 | DiMeo et al. | |
| 8,840,608 B2 | 9/2014 | Anderson et al. | |
| 8,974,451 B2 | 3/2015 | Smith | |
| 9,044,212 B2 | 6/2015 | LePivert | |
| 9,078,634 B2 | 7/2015 | Gonzales et al. | |
| 9,132,031 B2 | 9/2015 | Levinson et al. | |
| 9,314,368 B2 | 4/2016 | Allison et al. | |
| 9,345,526 B2 | 5/2016 | Elkins et al. | |
| 9,375,345 B2 | 6/2016 | Levinson et al. | |
| 9,398,930 B2 | 7/2016 | Leung et al. | |
| 9,408,745 B2 | 8/2016 | Levinson et al. | |
| 9,522,031 B2 | 12/2016 | Anderson et al. | |
| 9,545,523 B2 | 1/2017 | Nanda | |
| 9,585,687 B2 | 3/2017 | Tenenbaum et al. | |
| 9,649,220 B2 | 5/2017 | Anderson et al. | |
| 9,655,770 B2 | 5/2017 | Levinson et al. | |
| 9,656,056 B2 | 5/2017 | Boyden et al. | |
| 9,980,765 B2 | 5/2018 | Avram et al. | |
| 10,174,985 B2 | 1/2019 | Arnitz et al. | |
| 10,406,021 B2 | 9/2019 | Wu et al. | |
| 10,500,342 B2 | 12/2019 | Velis | |
| 2001/0005338 A1 | 6/2001 | Muhlbauer et al. | |
| 2002/0107199 A1 | 8/2002 | Walker | |
| 2003/0012079 A1 | 1/2003 | Coffeen et al. | |
| 2003/0032996 A1 | 2/2003 | Hallman | |
| 2003/0074903 A1 | 4/2003 | Upadhye et al. | |
| 2003/0171715 A1 | 9/2003 | Hommann et al. | |
| 2003/0220674 A1* | 11/2003 | Anderson ............. | A61B 18/02 607/96 |
| 2004/0073280 A1 | 4/2004 | Dae et al. | |
| 2004/0092883 A1 | 5/2004 | Casey et al. | |
| 2004/0092920 A1 | 5/2004 | Rozenshpeer | |
| 2004/0199115 A1 | 10/2004 | Rosenman | |
| 2004/0220559 A1 | 11/2004 | Kramer et al. | |
| 2004/0267338 A1 | 12/2004 | Harrison | |
| 2005/0203598 A1 | 9/2005 | Becker et al. | |
| 2005/0251120 A1 | 11/2005 | Anderson et al. | |
| 2006/0030843 A1 | 2/2006 | Lane et al. | |
| 2006/0036302 A1 | 2/2006 | Kasza et al. | |
| 2006/0122673 A1* | 6/2006 | Callister ............ | A61F 7/12 607/105 |
| 2006/0161232 A1 | 7/2006 | Kasza et al. | |
| 2006/0190066 A1 | 8/2006 | Worthen | |
| 2007/0010861 A1 | 1/2007 | Anderson et al. | |
| 2007/0056313 A1 | 3/2007 | Kasza et al. | |
| 2007/0106247 A1 | 5/2007 | Burnett et al. | |
| 2007/0198071 A1 | 8/2007 | Ting et al. | |
| 2007/0255362 A1 | 11/2007 | Levinson et al. | |
| 2007/0270925 A1 | 11/2007 | Levinson | |
| 2008/0045880 A1 | 2/2008 | Kjeken et al. | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0161772 A1 | 7/2008 | Nayak et al. | |
| 2008/0195114 A1 | 8/2008 | Murphy | |
| 2008/0236186 A1 | 10/2008 | Kasza et al. | |
| 2008/0287839 A1 | 11/2008 | Rosen et al. | |
| 2008/0300540 A1 | 12/2008 | Lewis | |
| 2009/0012497 A1 | 1/2009 | Uber, III et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0030366 A1 | 1/2009 | Hochman | |
| 2009/0071829 A1 | 3/2009 | O'Banion et al. | |
| 2009/0118722 A1 | 5/2009 | Ebbers et al. | |
| 2009/0125087 A1 | 5/2009 | Becker et al. | |
| 2009/0149929 A1 | 6/2009 | Levinson et al. | |
| 2009/0255276 A1 | 10/2009 | Kasza et al. | |
| 2009/0270814 A1 | 10/2009 | Masi et al. | |
| 2010/0036295 A1 | 2/2010 | Altshuler et al. | |
| 2010/0081971 A1 | 4/2010 | Allison | |
| 2010/0152824 A1 | 6/2010 | Allison | |
| 2010/0152880 A1 | 6/2010 | Boyden et al. | |
| 2010/0249753 A1 | 9/2010 | Gaisser et al. | |
| 2010/0274184 A1 | 10/2010 | Chun | |
| 2010/0280582 A1 | 11/2010 | Baker et al. | |
| 2010/0308257 A1 | 12/2010 | Lampe et al. | |
| 2010/0312202 A1 | 12/2010 | Henley et al. | |

(56) References Cited

U.S. PATENT DOCUMENTS

| | | |
|---|---|---|
| 2011/0066216 A1 | 3/2011 | Ting et al. |
| 2011/0190751 A1 | 8/2011 | Ingle et al. |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0000217 A1 | 1/2012 | Gudnason |
| 2012/0022518 A1 | 1/2012 | Levinson |
| 2012/0055187 A1 | 3/2012 | Raines et al. |
| 2012/0167878 A1 | 7/2012 | Belzon et al. |
| 2012/0203312 A1* | 8/2012 | Batzer ............... A61F 7/02 607/105 |
| 2012/0239123 A1 | 9/2012 | Weber et al. |
| 2012/0289761 A1 | 11/2012 | Boyden et al. |
| 2013/0066309 A1 | 3/2013 | Levinson |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0190744 A1 | 7/2013 | Avram et al. |
| 2013/0245731 A1 | 9/2013 | Allison |
| 2013/0253496 A1 | 9/2013 | Anderson et al. |
| 2013/0319080 A1 | 12/2013 | Sezaki et al. |
| 2014/0005760 A1 | 1/2014 | Levinson et al. |
| 2014/0067025 A1 | 3/2014 | Levinson et al. |
| 2014/0091113 A1 | 4/2014 | Brewster et al. |
| 2014/0200511 A1 | 7/2014 | Boyden et al. |
| 2014/0257443 A1 | 9/2014 | Baker et al. |
| 2014/0277219 A1 | 9/2014 | Nanda |
| 2014/0277302 A1 | 9/2014 | Weber et al. |
| 2014/0303608 A1 | 10/2014 | Taghizadeh |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0358079 A1 | 12/2014 | Fischell et al. |
| 2014/0378937 A1 | 12/2014 | Anderson et al. |
| 2015/0080769 A1 | 3/2015 | Lotsch |
| 2015/0112195 A1 | 4/2015 | Berger et al. |
| 2015/0141916 A1 | 5/2015 | Albrecht et al. |
| 2015/0216816 A1 | 8/2015 | O'Neil et al. |
| 2015/0297246 A1 | 10/2015 | Patel et al. |
| 2015/0320938 A1 | 11/2015 | King et al. |
| 2015/0328077 A1 | 11/2015 | Levinson |
| 2015/0342780 A1 | 12/2015 | Levinson et al. |
| 2015/0343156 A1 | 12/2015 | Fischell et al. |
| 2016/0051401 A1 | 2/2016 | Yee et al. |
| 2016/0058956 A1 | 3/2016 | Cohn et al. |
| 2016/0081974 A1 | 3/2016 | Lee et al. |
| 2016/0089550 A1 | 3/2016 | DeBenedictis et al. |
| 2016/0112195 A1 | 4/2016 | Jochheim et al. |
| 2016/0128767 A1 | 5/2016 | Azamian et al. |
| 2016/0175141 A1 | 6/2016 | Wu et al. |
| 2016/0184568 A1 | 6/2016 | Harris et al. |
| 2016/0242661 A1 | 8/2016 | Fischell et al. |
| 2016/0317621 A1 | 11/2016 | Bright |
| 2016/0354137 A1 | 12/2016 | Fischell et al. |
| 2016/0354237 A1 | 12/2016 | Gonzales et al. |
| 2017/0035603 A1 | 2/2017 | Kammer et al. |
| 2017/0051353 A1 | 2/2017 | Eng |
| 2017/0105869 A1 | 4/2017 | Frangineas, Jr. |
| 2017/0136237 A1 | 5/2017 | Eckhouse et al. |
| 2017/0143538 A1 | 5/2017 | Lee et al. |
| 2017/0164965 A1 | 6/2017 | Chang et al. |
| 2017/0202613 A1 | 7/2017 | Pellegrino et al. |
| 2017/0246032 A1 | 8/2017 | Gonzales et al. |
| 2017/0274011 A1 | 9/2017 | Garibyan et al. |
| 2017/0274078 A1 | 9/2017 | Garibyan et al. |
| 2017/0325992 A1 | 11/2017 | DeBenedictis et al. |
| 2018/0008500 A1 | 1/2018 | Anderson et al. |
| 2018/0116868 A1 | 5/2018 | Velis et al. |
| 2018/0140514 A1 | 5/2018 | Velis et al. |
| 2018/0289537 A1 | 10/2018 | Velis |
| 2018/0311079 A1 | 11/2018 | Garibyan et al. |
| 2019/0053939 A1 | 2/2019 | Garibyan et al. |
| 2019/0054242 A1 | 2/2019 | Velis |
| 2020/0046552 A1 | 2/2020 | Velis et al. |
| 2020/0086054 A1 | 3/2020 | Velis |
| 2020/0113627 A1 | 4/2020 | Alas et al. |
| 2020/0114041 A1 | 4/2020 | Alas et al. |

FOREIGN PATENT DOCUMENTS

| | | |
|---|---|---|
| CN | 103110473 A | 5/2013 |
| CN | 104010598 | 8/2014 |
| CN | 105640706 A | 6/2016 |
| EP | 0418979 A2 | 3/1991 |
| EP | 0 445 951 | 9/1991 |
| ES | 2 421 545 | 9/2013 |
| GB | 2 338 428 | 12/1999 |
| JP | 2003-500097 | 1/2003 |
| JP | 2008-529663 | 8/2008 |
| JP | 2009-539575 | 11/2009 |
| WO | 2006/086479 | 8/2006 |
| WO | 2009/086399 A2 | 7/2009 |
| WO | 2009/089090 | 7/2009 |
| WO | 2013/036540 | 3/2013 |
| WO | 2013/113970 | 8/2013 |
| WO | 2016/033380 A1 | 3/2016 |
| WO | 2016/033384 A1 | 3/2016 |
| WO | 2016/054165 | 4/2016 |
| WO | 2016/090175 A1 | 6/2016 |
| WO | 2016/138045 | 9/2016 |
| WO | 2017/147367 A1 | 8/2017 |
| WO | 2017/196548 A1 | 11/2017 |
| WO | 2018/187573 A1 | 10/2018 |

OTHER PUBLICATIONS

Extended European Search Report dated Dec. 16, 2020 in corresponding European Application No. 18781069.2.

Extended European Search Report dated Dec. 9, 2020 in European Application No. 18781693.9.

Search Report and Written Opinion dated Feb. 17, 2021 in Singapore Application No. 11201909303T, with English translation.

Search Report and Written Opinion dated Feb. 8, 2021 in Singapore Application No. 11201909305P, with English translation.

Extended European Search Report dated Aug. 28, 2020 in European Application No. 17868153.2.

Written Opinion dated Jul. 1, 2020 in Singapore Application No. 11201903946S.

International Preliminary Report on Patentability dated Aug. 21, 2012, for International application No. PCT/US2011/024766, filed Feb. 14, 2011 (8 pages).

International Search Report, Written Opinion of the International Searching Authority, and Search Strategy for PCT/US2018/026273, dated Aug. 29, 2018, 15 pages.

Ash, 2003, Chronic peritoneal dialysis catheters: overview of design, placement, and removal procedures, Int Nephrol Dialysis 16(4):323-34.

Brink, 2008, Abdominoplasty with direct resection of deep fat, Plast Reconstructive Surg 123(5):1597-1603.

Ding, 2008, The association between non-subcutaneous adiposity and calcified coronary plaque: A substudy of the multi-ethnic study of atherosclerosis, Am J Clin Nutr 88(3):645-650.

Esposito, 2016, Do you know this syndrom? Type 2 benign symmetric lipomatos (Launois-Bensaude), Brazilian Annals of Dermatology 91:841.

Fox, 2007, Abdominal visceral and subcutaneous adipose tissue compartments—association with metabolic risk factors in the Framingham heart study, Circulation 116:39-48.

Garaulet, 2006, Relationship between fat cell size and number and fatty acid composition in adipose tissue from different fat depots in overweight/obese humans, Int J Obes 30(6):899-905.

Gentile, 2016, Lipodystrophy in Insulin-Treated Subjects and Other Injection-Site Skin Reactions: Are we Sure Everything is Clear?, Diabetes Therapy 7.

Gradinger, 2005, Abdominoplasty, Chapter 83, pp. 2935-3026, in The art of aesthetic surgery: principles & techniques, Nahai, Ed., Quality Med Pub, St. Louis Mo. (92 pages).

(56) References Cited

OTHER PUBLICATIONS

Int Search Report & Written Opinion dated Apr. 12, 2011, for PCT/US11/24766, filed Feb. 14, 2011 (11 pages).
Int Search Report & Written Opinion dated Dec. 11, 2019 for International Application No. PCT/ US2019/054828.
Int Search Report & Written Opinion dated Dec. 23, 2019, for PCT/US19/54834, filed Oct. 4, 2019 (10 pages).
Int Search Report & Written Opinion dated Feb. 11, 2020, for PCT/US19/55633, filed Oct. 10, 2019 (12 pages).
Int Search Report & Written Opinion dated Jan. 2, 2020, for PCT/US19/55605, filed Oct. 10, 2019 (9 pages).
Int Search Report & Written Opinion dated Jun. 11, 2018, for PCT/US2018/026260, filed Apr. 5, 2018 (6 pages).
Int Search Report & Written Opinion dated May 15, 2018, for PCT/US17/59947, filed Nov. 3, 2017 (8 pages).
Int Search Report & Written Opinion dated May 7, 2018, for PCT/US18/20387, filed Mar. 1, 2018 (7 pages).
Kanamori, 2015, A case of an 8-year-old boy who was strongly suspected of suffering from familial angiolipomatosis, J Pediatric Surg 3.
Kosseifi, 2010, Dercum's Disease: An Unusual Presentation, Pain Medicine 11:1432.
Laven, 2006, A pilot study of ice-slurry application for inducing laparoscopic renal hypothermia, BJU Int 99:166-70.
Laverson, 2006, Improving abdominoplasty results: reconstruction of the linea alba sulcus by direct excision, Aesthetic Surg J 26:682-6.
Lv, 2017, A review of the postoperative lymphatic leakage, Oncotarget 8:69069.
Popescu, 2014, Proteus Syndrome: a difficult diagnosis and management plan, J Med and Life 7:1.
Stevens, 2014, Does cryolipolysis lead to skin tightening? A first report of cryodermadstringo, Aesth Surg J 34(6):NP32-NP34.
Yamamoto, 2010, Adipose depots possess unique developmental gene signatures, Obesity 18(5):872-78.

* cited by examiner

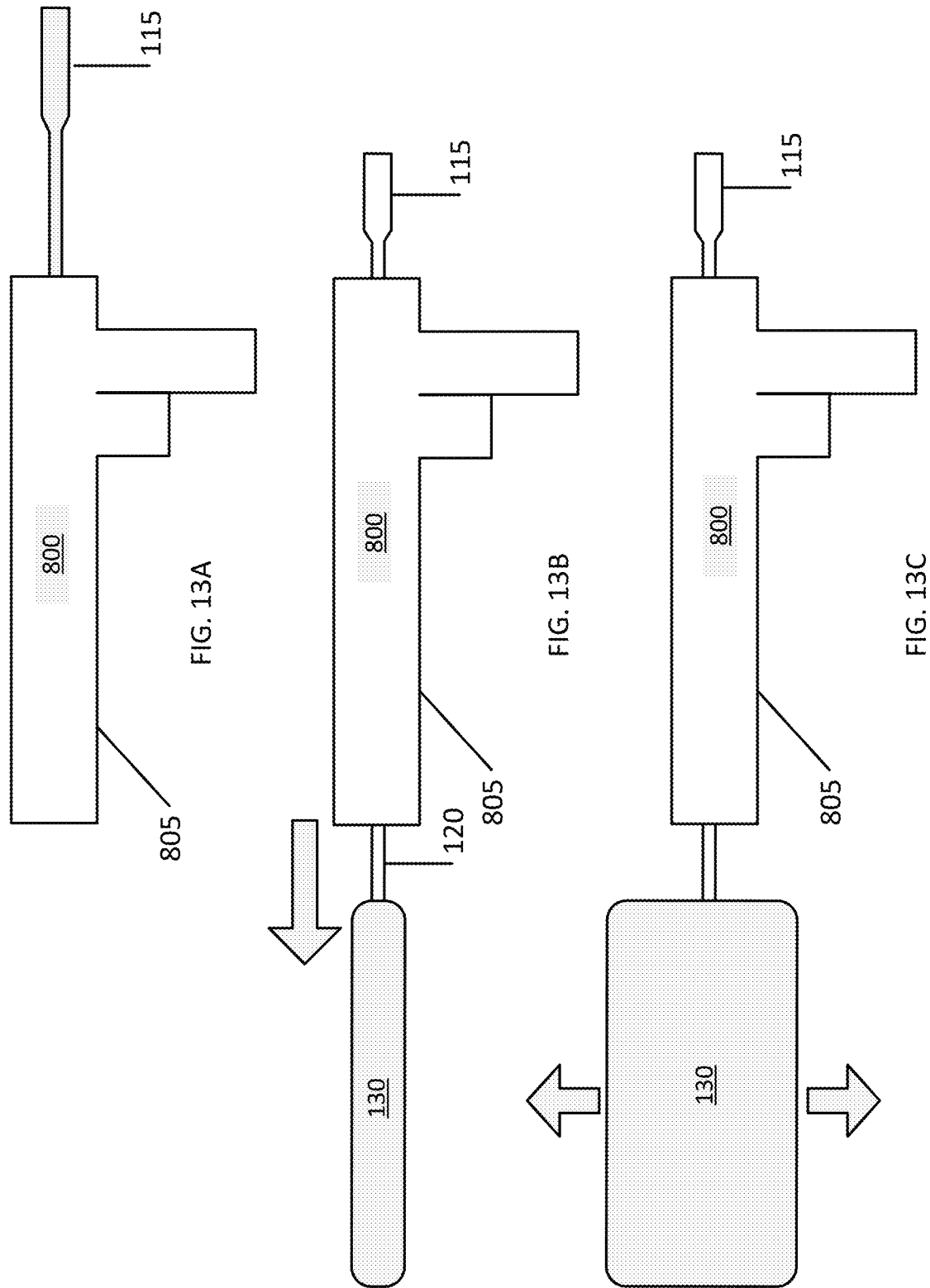

COLD SLURRY CONTAINMENT

CROSS REFERENCE TO RELATED APPLICATIONS

This application claims the benefit under 35 U.S.C. § 119(e) of U.S. Provisional Application Ser. No. 62/482,008 filed on Apr. 5, 2017 the entire disclosure of which is incorporated herein by reference.

BACKGROUND

Cold slurries used in medical applications typically comprise a partially frozen saline solution. Cold slurries are used in surgical applications to induce therapeutic hypothermia and slow organ and tissue metabolic rates thereby protecting a patient's organs during a surgical procedure. Cold slurries can also be injected into a patient for selective or non-selective cryotherapy and/or cryolipolysis.

Approaches to preparing and delivering a cold slurry to fat tissue through a cannula or needle are disclosed in International Application No. PCT/US2015/047292; U.S. Patent Application Publication No. 2013/0190744; and U.S. Provisional Application No. 62/416,484, which are incorporated herein by reference in their entirety. A cold slurry has high fluidity making to possible to inject the cold slurry through a small cannula or needle. Once the cold slurry is delivered, heat transfers from the target tissue to the cold slurry. This lowers the temperature of the target tissue, so that cryolipolysis can occur.

Because the cold slurry is highly fluid, it tends to spread out from where it is delivered to surrounding tissue. A three cubic centimeter volume of cold slurry can cover an area that is about the size of a saucer plate. Heat from the surrounding tissues is also transferred to the cold slurry. Additionally, blood flowing into the treatment area can warm the cold slurry. As more heat is transferred to the cold slurry, the ability for the cold slurry to lower the tissue temperature of the target tissue decreases. Consequently, more cold slurry may be needed for an effective treatment. Another challenge to delivering a cold slurry is protecting tissue surrounding the target tissue from the cooling effects of the cold slurry.

SUMMARY

The present invention provides methods and devices for controlling a cold slurry that is delivered to a target tissue and for limiting heat transferring from surrounding tissue to the target tissue. In particular, a balloon structure is deployed at or near a point of delivery to act as a physical and/or thermal barrier. In some instances, the balloon can act as a pressure device obstructing the flow of blood into a treatment area, which can melt the cold slurry.

A balloon structure for use in the invention can take various forms and shapes, and can have chambers that can be opened or closed to control the shape of the balloon. In some examples, balloons are nested within each other and filled with various fluids or gasses of varying temperatures. For example, in one embodiment, a first inner balloon is filled with a cool mix of water and glycerol, and a second inner balloon, which encloses the first inner balloon, is filled with a coolant gas/fluid (e.g., liquid nitrogen) to freeze or chill the cool mix in the first inner balloon. There can even be a third balloon, which encloses the second inner balloon. The third balloon is filled with a thermal insulator, such as air, to protect surrounding tissue from the cold temperatures of the first and second inner balloons. The multiple balloons can be filled at the same time or at separate times.

A deployment device can be used to deploy the balloon. The device can have one or more working channels to control the function of the balloon or a collection of balloons. For example, the device has an application cannula for deploying multiple balloons one within the other, or one next to each other. In some examples, multiple balloons can be put to use with a set of deployment devices.

One aspect of the invention includes methods of controlling tissue temperature. Preferred methods include delivering a cold slurry to a target tissue located underneath a subject's skin. The target tissue is cooled to a lower tissue temperature as heat is transferred from the target tissue to the cold slurry. Methods further include limiting heat transfer from the surrounding tissue to the target tissue, which in turn slows down rising tissue temperature. Heat transfer can be limited using, for example, a balloon filled with a thermal insulator, such as a fluid, gas or air. The fluid/gas filled balloon acts as a barrier (or block) between the cold slurry and the surrounding tissue. The fluid/gas filled balloon can also act as a pressure device that exerts pressure against the surrounding tissue. The pressure exerted can constrict a blood vessel in the surrounding tissue and limit warm blood from flowing into the treatment area.

Another aspect of the invention is a device for carrying out the above approach. Preferred devices include a first cannula for delivering a cold slurry to a target tissue underneath a patient's skin, thereby cooling the target tissue. The first cannula includes a first open distal end and a first proximal end in fluid communication with a source of cold slurry. Devices further include a second cannula having a second open distal end and a second proximal end in fluid communication with a source of a thermal insulator. Devices further include a balloon disposed around the second open distal end of the second cannula. The balloon is positioned at or near tissue surrounding the target tissue. The balloon has a volume that is filled with the thermal insulator that has been delivered through second cannula. The filled balloon limits heat from transferring from the surrounding tissue to the target tissue.

The balloon can have a first chamber facing the target tissue and a second chamber facing the surrounding tissue. The first chamber is in fluid communication with the first open distal end and is filled with cold slurry delivered through the first cannula. The second chamber is in fluid communication with the second open distal end and is filled with the thermal insulator delivered through the second cannula. This configuration cools the target tissue while projecting the surrounding tissue.

Some devices have two balloons. A first balloon is disposed around the first open distal end of the first cannula and positioned at or near the target tissue. The first balloon has a volume for receiving the cold slurry delivered through the first cannula. A second balloon is disposed around the second open distal end of the second cannula. The second has a volume filled with the thermal insulator. The first balloon contains the cold slurry within its volume while the second balloon, positioned at or near tissue surrounding the target tissue, limits heat from transferring from the surrounding tissue to the target tissue.

Yet another aspect of the invention is a containment device that is applied over a patient's skin to limit/control the spread of cold slurry and/or its cooling effect from outside the patient's body. The containment device has an opening that defines a containment zone within which the cold slurry and/or its cooling effect is confined. The opening is surrounded by a pressure surface for applying pressure around the containment zone. Preferred devices include a pressure surface that is a hollow inside and that can expand when filled with a fluid or gas, such as air. Force is exerted by pumping air/fluid into the pressure surface causing it to expand and press against the patient's skin. The target tissue experiences little or no pressure because of the opening. The surrounding tissue, on the other hand, experiences positive pressure. This positive pressure limits the spread of cold slurry and/or its cooling effect from the target tissue to the surrounding tissue. Additionally, the pressure exerted by the containment device can constrict blood vessels in the surrounding tissue and limit warm blood from flowing into the treatment area.

Some containment devices can have a pressure surface that is divided into segments, for example, concentric rings. The segments can be filled, individually, such that the pressure exerted by each segment is different. For example, a first segment closest to the opening is filled so that the pressure exerted against the patient's skin is greater than the pressure exerted by a second segment. The difference in pressure applied by the containment device can help control the migration of cold slurry. Additional, the different pressures exerted by the containment device segments can facilitate tissue contouring.

Still yet another aspect of the invention is a warm fluid removal device for removing melted cold slurry from the treatment area. Preferred devices have a distal end that is positioned a distance away for the target tissue and within the surrounding tissue. The devices further include a proximal end that is coupled to a vacuum pump that provides the suction to remove the warm fluid from the treatment area. The vacuum pump is operatively coupled to a controller for operating the vacuum pump. The controller can operate the vacuum pump continuously or intermittently. The controller can also monitor the temperature of the target tissue using a temperature probe and operate the warm fluid removal device in response to the rising tissue temperature.

Example warm fluid removal devices can be U-shaped and surround the target tissue when in use. These devices have a plurality of holes defined along their length through which warm fluid is removed from the treatment area. The warm fluid removal devices can also include an open distal end to further enhance removing warm fluid from the treatment area. These devices can further have a non-operating mode and an operating mode. In the non-operating mode, the warm fluid removal device is substantial linear in shape. In the non-operating mode, the warm fluid removal device can be readily inserted through the patient's skin, advanced to the tissue surrounding the target tissue, and removed from the patient when the cold slurry treatment is done. In the operating mode, the warm fluid removal device is U-shaped with the open end facing the target tissue. The warm fluid removal device can be mechanically actuated between the non-operating mode and operating mode with a tension wire, for example. In another example, the warm fluid removal device is made for a shape memory alloy, such as nitinol. The warm fluid removal device can change from the linear shape to the U-shape, and back to the linear shape in response to changes in temperature.

BRIEF DESCRIPTION OF DRAWINGS

FIGS. 13A-13C are views of an example guide for deploying a cold slurry containment device.

DETAILED DESCRIPTION

Figure 1:
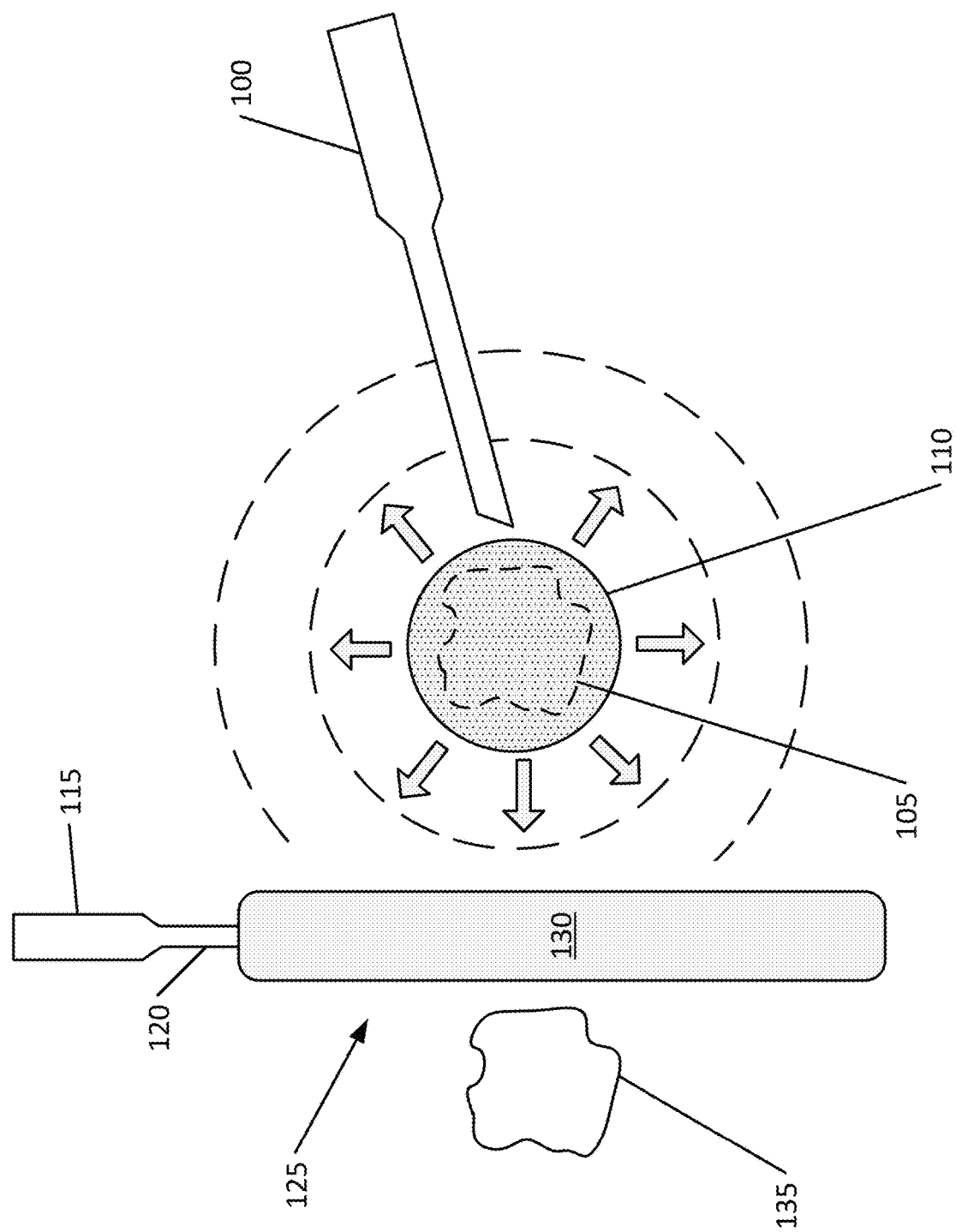
FIG. 1 is a diagram of an approach to delivering a cold slurry and controlling its migration and/or cooling effect.

FIG. 1 shows a cold slurry being injected into a patient. A cold slurry delivery device 100 having a cannula is inserted through the patient's skin and advanced to a location at or near a target tissue 105 (shown in phantom line). A cold slurry 110 is then delivered. Heat from the target tissue 105 is transferred to the cold slurry 110, which in turn lowers the temperature of the target tissue 105. After delivery, an area affected by the cold slurry 110 expands to a size larger than the initial delivery site (shown in the figure as arrows radiating outwardly from the delivered cold slurry 110 and dashed circles of increasing size).

FIG. 1 further shows an approach for controlling the cooling effect of the cold slurry 110. A deployment device 115 having an application cannula 120 is inserted through the patient's skin. At the distal end of the application cannula 120, there is a controlling end 125. The deployment device 115 is advanced until the controlling end 125 is at a location between the target tissue 105 and an adjacent (surrounding) tissue 135. The controlling end 125 includes a balloon 130. While the balloon 130 is shown having a linear shape, it can have any shape, such as a ring that encircles the target tissue 105. The balloon 130 is filled with air to create a barrier between the adjacent tissue 135 and the spreading cold slurry 110. The balloon 130 limits heat transferring from the adjacent tissue 135 to the cold slurry 110.

Figure 2:
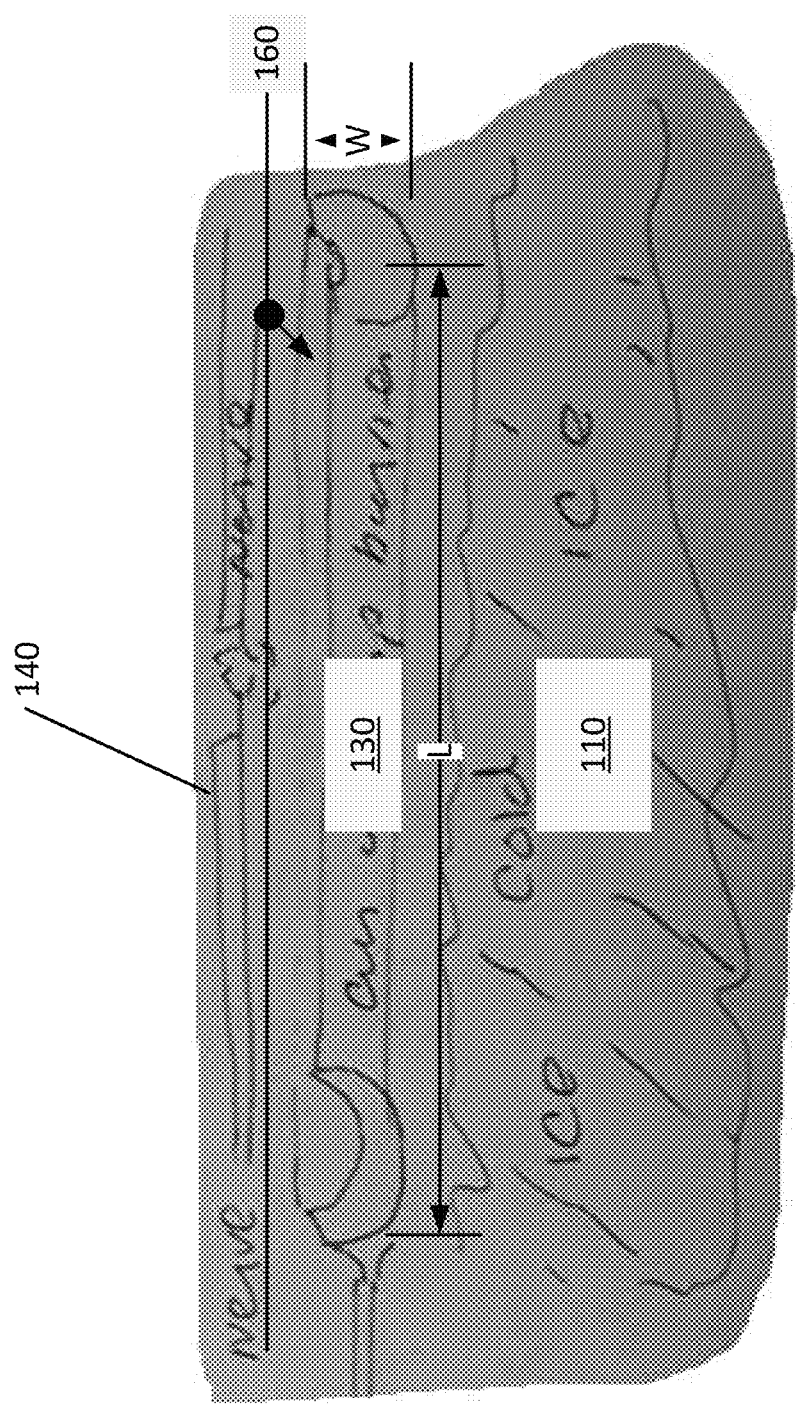
FIG. 2 is a side view of a balloon acting as a thermal barrier protecting a nerve from the cooling effect of the cold slurry.

The approach provides several benefits. By acting as a temperature barrier, the balloon 130 can slow down the melting process, thereby prolonging the usefulness of the cold slurry 110. The balloon 130 can further help keep the target tissue 105 cold and thus, increase the effectiveness of the cold slurry treatment. By acting as a temperature barrier, the balloon 130 also protects the adjacent tissue 135 from being adversely affected or damaged by the cold. For example, FIG. 2 shows the balloon 130 placed between the cold slurry 110 and a nerve 140. The balloon 130 limits the cooling effect of the cold slurry 110 on the nerve 140. Beneficially, this lowers the possibility of damaging the nerve 140.

Figure 3:
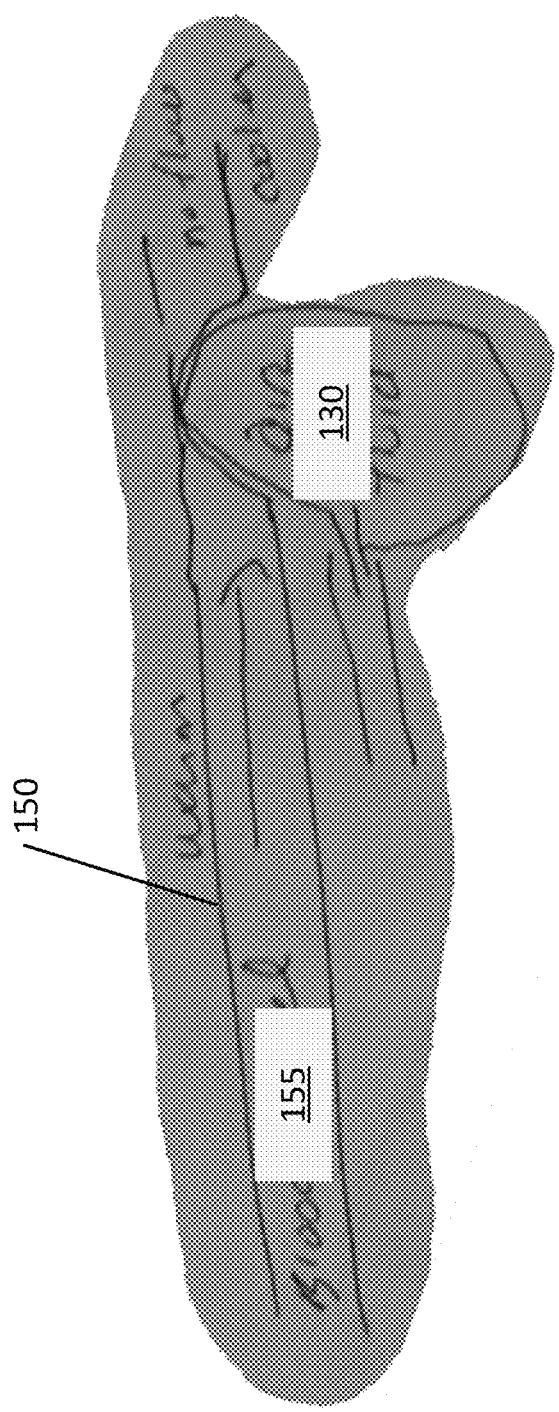
FIG. 3 is a side view of a balloon acting as a pressure device limiting blood flow into a treatment area.

FIG. 3 shows another application of the balloon 130. The balloon 130 filled with air or fluid is placed next to a blood vessel 150. The balloon 130 exerts pressure on the blood vessel 150 causing it to constrict and limit blood flow 155, as shown. By reducing the amount of warm blood flowing into a treatment area, the balloon 130 can slow down the melting process, thereby prolonging the usefulness of cold slurry. The balloon 130 can further help keep a target tissue cold and thus, increase the effectiveness of the cold slurry treatment.

Figure 4:
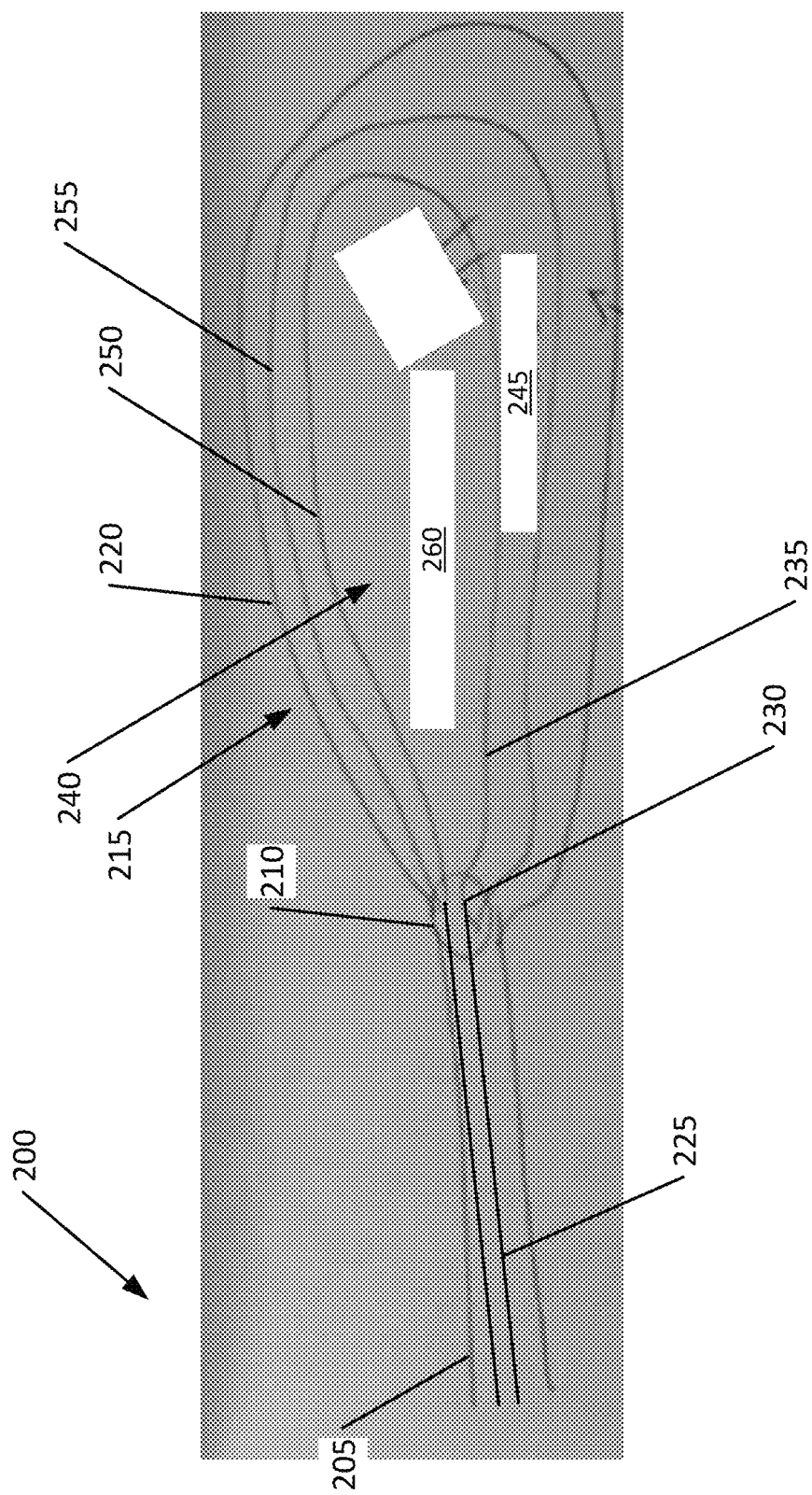
FIG. 4 is a sectional view of a cold slurry delivery device.

FIG. 4 shows an example cold slurry delivery device 200. The device 200 includes an application cannula 205 that is open at its distal end and defines an outlet 210. A controlling end 215 includes an outer balloon 220 disposed around the outlet 210. The application cannula 205 is in fluid communication with the interior volume of the outer balloon 220. The application cannula 205 includes a fluid delivery cannula 225. The application cannula 205 and the fluid delivery cannula 225 share a common longitudinal axis and can be said to be coaxial aligned.

The fluid delivery cannula 225 is open at its distal end defining a fluid outlet 230. The controlling end 215 further includes an inner balloon 235 disposed around the fluid outlet 230. The fluid delivery cannula 225 is in fluid communication with an interior volume of the inner balloon 235, which is labeled 240 in the figure. The inner balloon 235 is located inside the outer balloon 220. As shown, the inner balloon 235 occupies a portion of the interior volume of the outer balloon 220 leaving a space or gap 245 between an outer wall of the inner balloon 235 (which is labeled 250 in the figure) and an inner wall of the outer balloon 220 (which is labeled 255 in the figure).

To use the cold slurry delivery device 200, the application cannula 205 is inserted through the patient's skin and the controlling end 215 is advanced to a location at or near a target tissue in much the same manner as described above with reference to FIG. 1. In this example, the outer balloon 220 and the inner balloon 235 are inserted into the patient's body in their uninflated state. The outer balloon 220 is filled with air that is supplied through the application cannula 205. The inner balloon 235 is filled with a cold slurry 260 that is supplied through the fluid delivery cannula 225. The air filling the gap 645 between the inner balloon 235 and the outer balloon 220 acts an insulator and protects the surrounding tissue from damage. The inner balloon 235 can also be filled with a fluid, gel, inorganic aerogel, foam or other thermal insulator.

Figure 5:
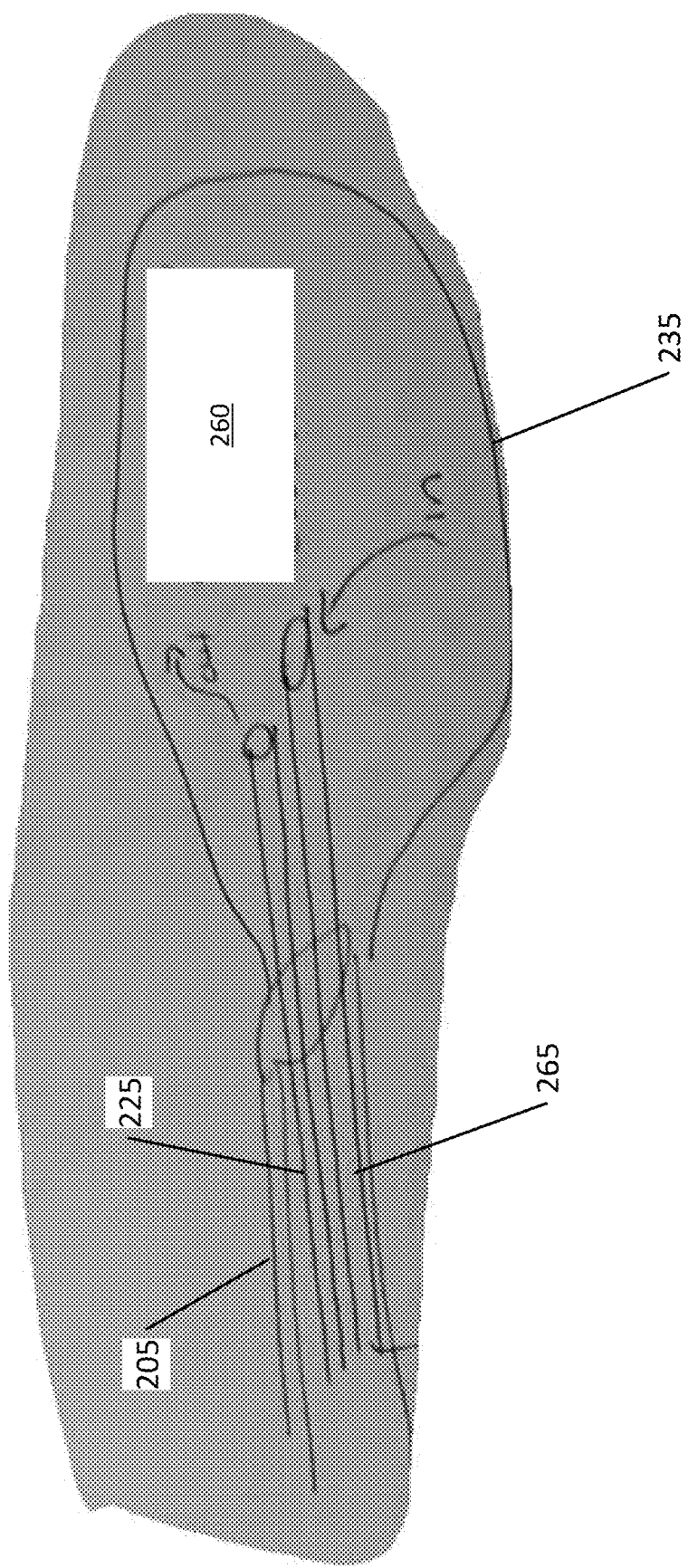
FIG. 5 is a view of a cold slurry delivery device for delivering and replenishing cold slurry.

FIG. 5 shows another example of the cold slurry delivery device 200 for delivering a cold slurry. This example is similar to the one described above with reference to FIG. 4 with the addition of a fluid return cannula 265. The fluid return cannula 265 is housed within the application cannula 205 together with the fluid delivery cannula 225, as shown. The fluid return cannula 265 removes cold slurry from the inner balloon 235 that is no longer at the desired temperature. Replenishing the "old" cold slurry with "fresh" cold slurry in this manner can accommodate for the eventually melting of cold slurry. This approach is particular useful for a treatment that requires a long period of cooling.

Figure 6:
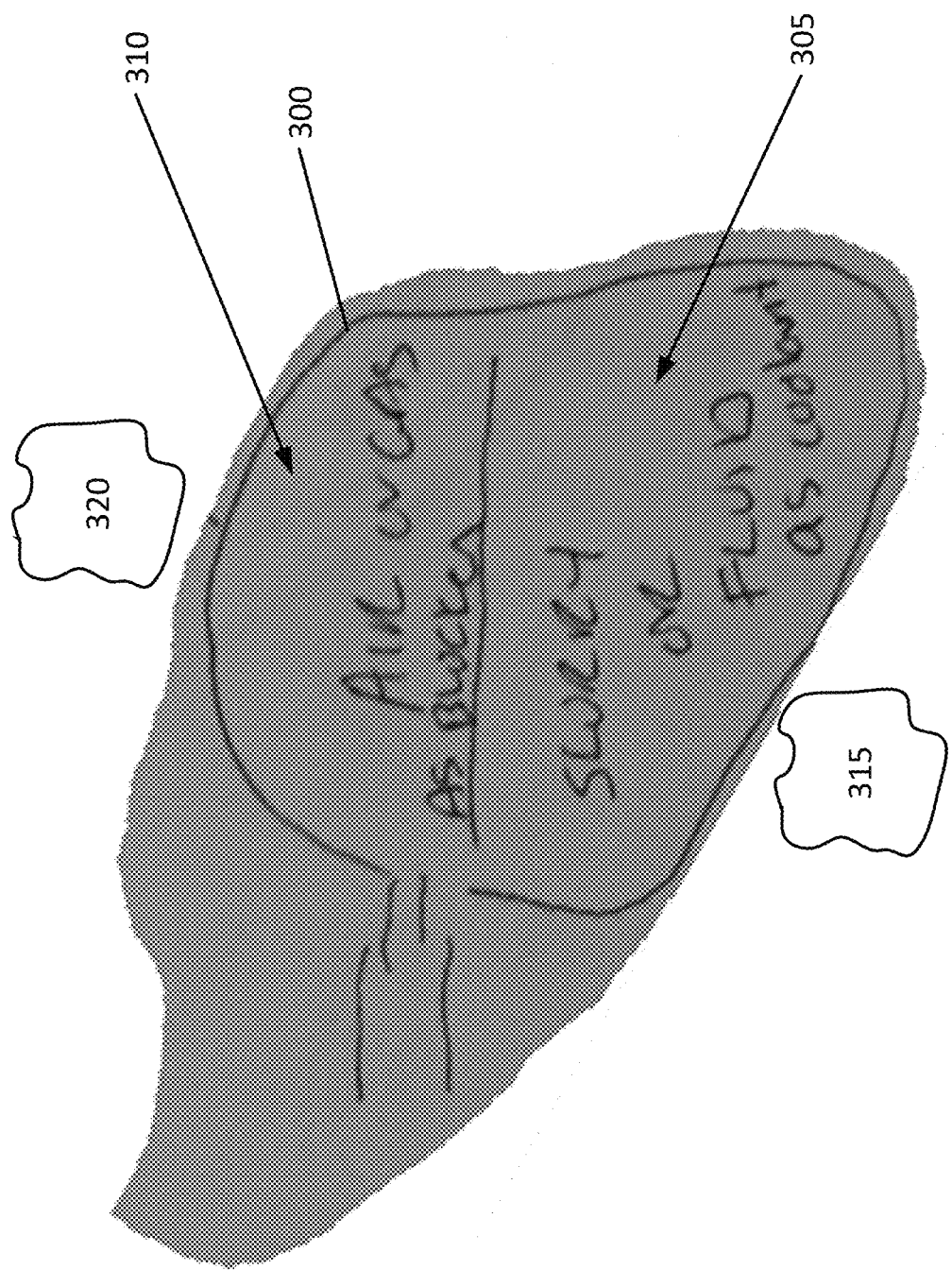
FIG. 6 is a sectional view of a two-chamber balloon for delivering cold slurry to a target tissue and protecting an adjacent tissue from the cooling effect of the cold slurry.
Figure 7:
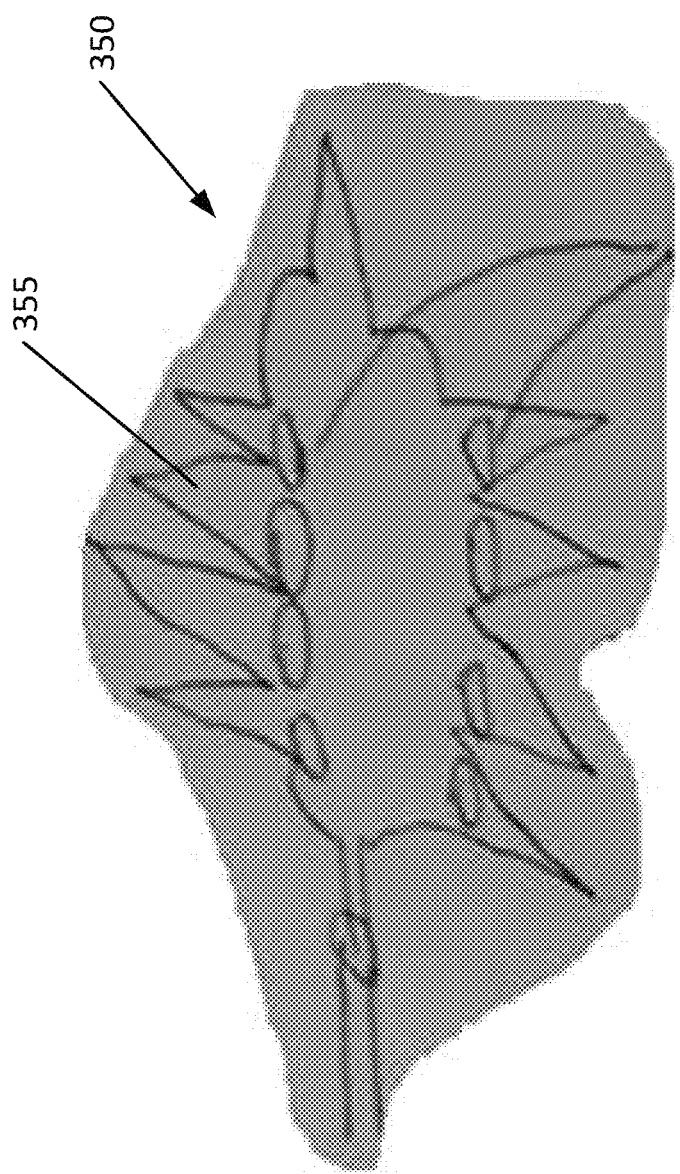
FIG. 7 is a view of an example balloon having projecting arms.

FIG. 6 shows an example balloon 300 for delivering cold slurry. The balloon 300 has a first chamber 305 and a second chamber 310, as shown. The first chamber 305 is filled a cold slurry (or other cooling fluid) and faces a target tissue 315. The second chamber 310 is filled with air (or other gas) and faces an adjacent tissue 320, which is near the target tissue 315. This configuration allows the balloon 300 to cool the target tissue 315 while protecting the adjacent tissue 320 from the cooling effect of the cold slurry. Examples of the balloon can have any shape in addition to the linear and spherical examples described above with reference to FIGS. 1-5. For example, FIG. 2 shows the balloon 130 having a length (L) greater than its width (W) and having a concave shape. The point of concavity is defined by a point along an axis offset and parallel to a longitudinal axis 165. As another example, FIG. 7 shows a balloon 350 with several projecting arms or balusters 355.

Figure 8:
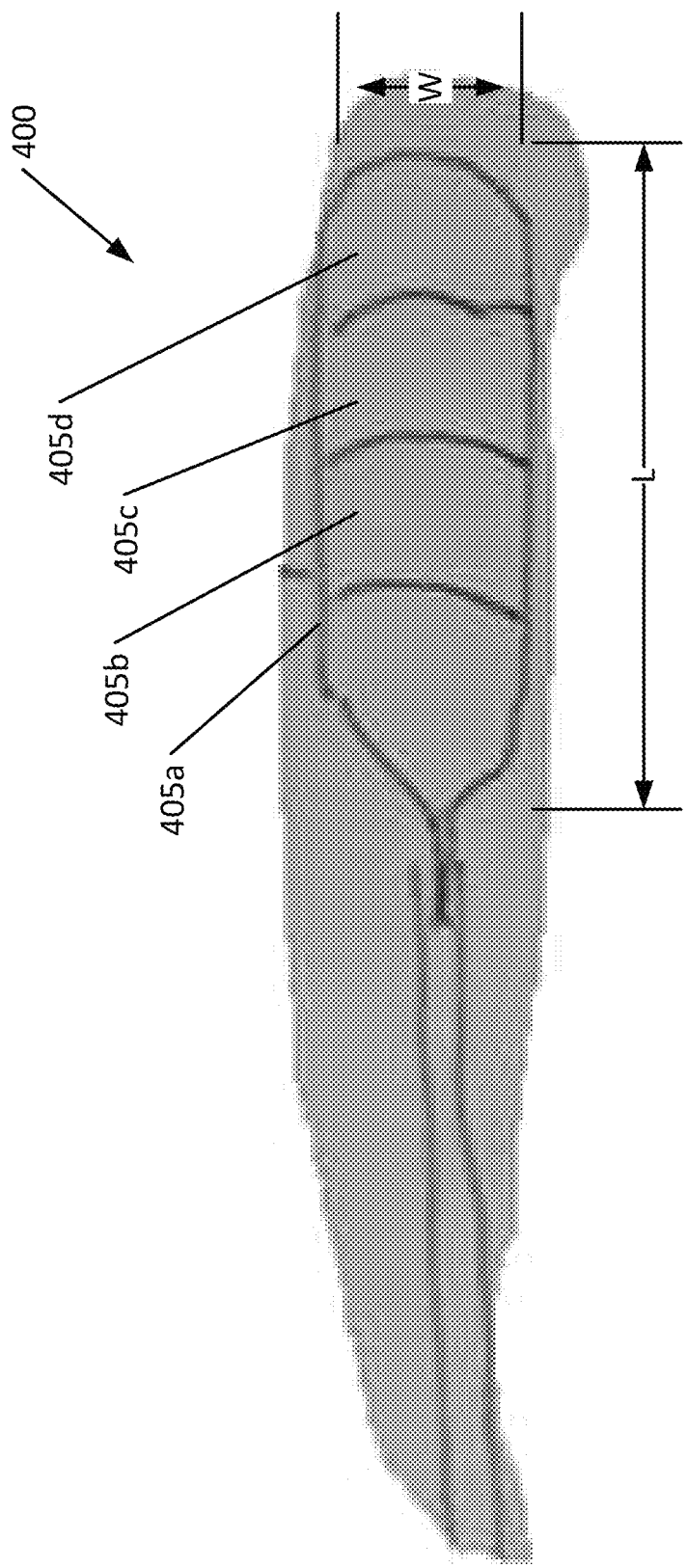
FIG. 8 is a view of an example balloon having multiple compartments.

Other examples of the balloon can have a number of chambers that can be opened or closed to control the shape of the balloon. For example, FIG. 8 shows a balloon 400 with four compartments 405a-405d (generally 405). The compartments 405 can be filled with various fluids or gasses of varying temperatures. The balloon 400 has a length (L) greater than its width (W).

Figure 9:
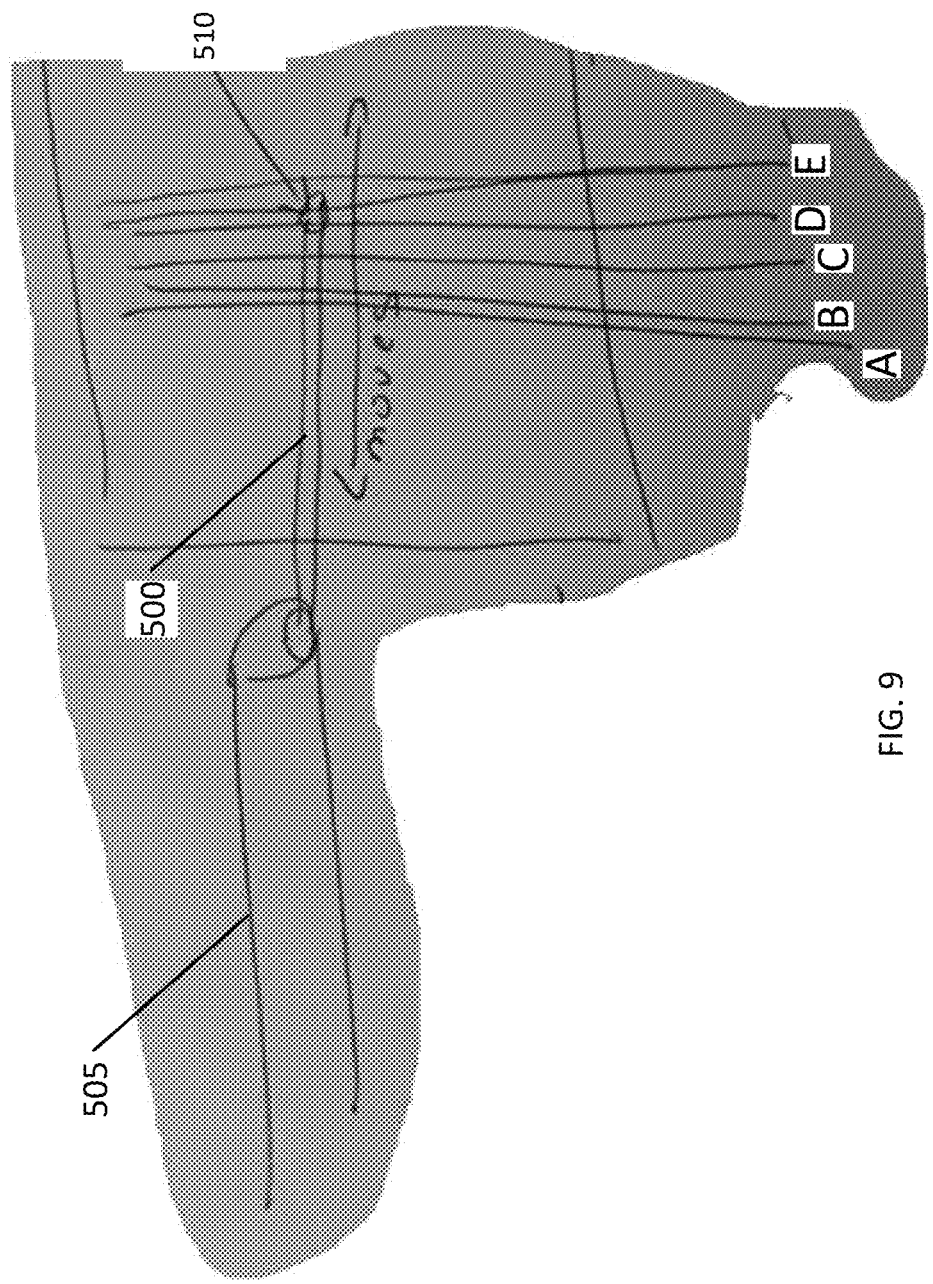
FIG. 9 is a view of an example cold slurry temperature monitor.

FIG. 9 shows a cold slurry temperature monitor 500 for measuring the temperature of the cold slurry. The cold slurry temperature monitor 500 can be a standalone device or incorporated with the cold slurry delivery device 100, 200 (of FIGS. 1 and 5) or the deployment device 115 (of FIG. 1). As shown, for example, the cold slurry temperature monitor 500 extends from an application cannula 505 (e.g., the cannula of the cold slurry delivery device 100). The cold slurry temperature monitor 500 can move between an extended position, which is shown in the figure, and a retracted position. In the retracted position, the cold slurry temperature monitor 500 is shielded within the application cannula 505. This helps with inserting the cold slurry temperature monitor 500 through the patient's skin and advancing the monitor 500 to a location at or near the cold slurry.

In the example shown, the cold slurry temperature monitor 500 includes at a temperature sensor 510 at its distal tip. Without limiting the principles of the invention, the temperature sensor 510 can be a forward infrared (FIR) sensor. As shown, the cold slurry temperature monitor 500 can be moved to intermediate positions between the retracted and extended positions. These intermediate positions together with the extended position correspond to different locations within the cold slurry, which are labelled in figure "A" through "E". By moving the cold slurry temperature monitor 500 to the intermediate positions and the extended position, a temperature gradient (or "temperature thru depth") of the cold slurry can be determined. The temperature gradient, in turn can, can be used to assess, for example, the capacity (capability) for the cold slurry to cool the target tissue.

Figure 10:
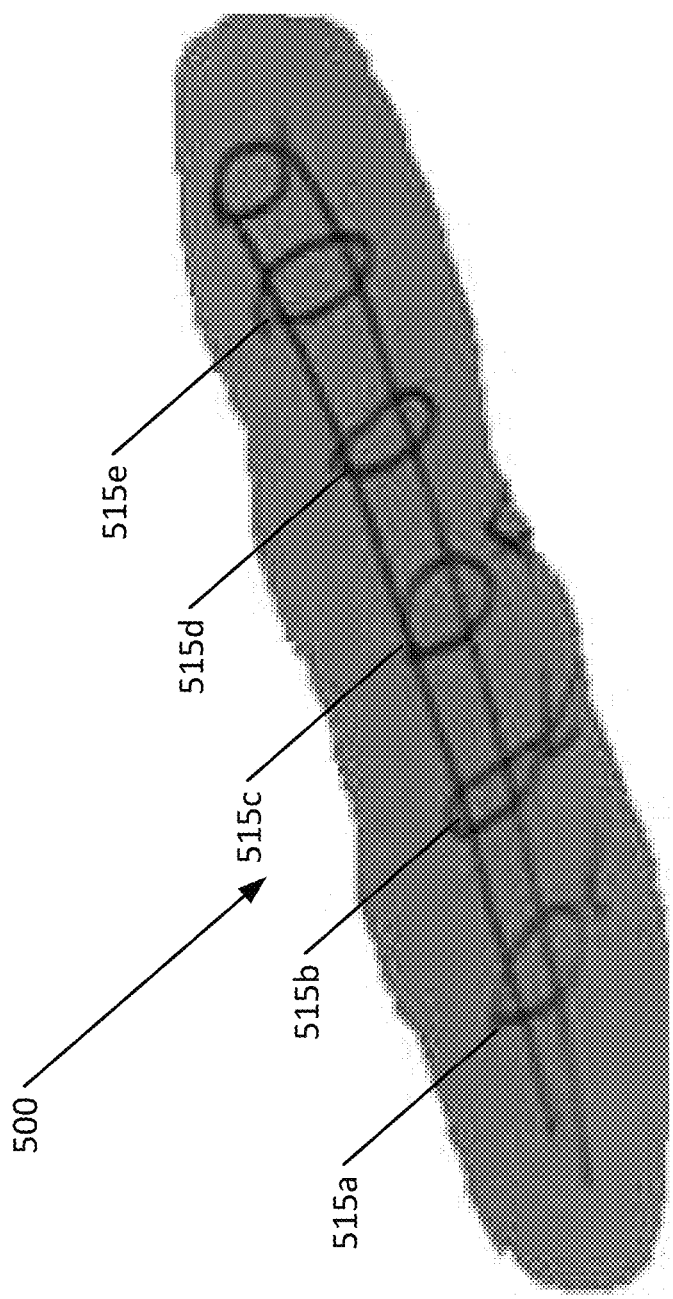
FIG. 10 is a view of an example cold slurry temperature monitor with multiple temperature sensors.

FIG. 10 shows another example of the cold slurry temperature monitor 500 having multiple sensors 515a-e (generally 515) spaced along the length of the monitor 500. Each of the sensors 515 measures a different location within the cold slurry. For example, sensor 515c measures the temperature of the cold slurry at the location labelled "C" in FIG. 9. In this way, a temperature gradient of the cold slurry can be determined without having to move the cold slurry temperature monitor 500.

Figure 11A:
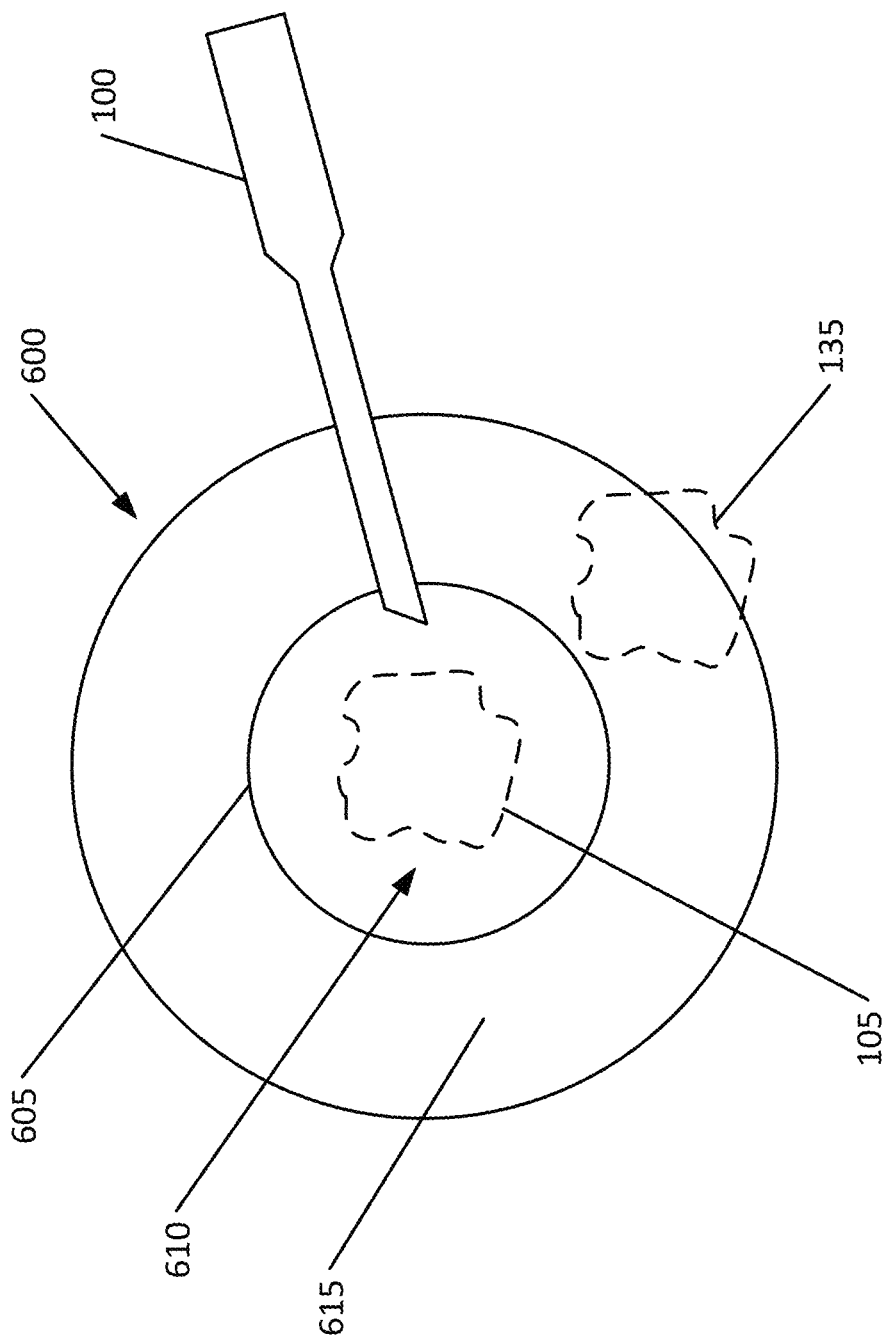
FIGS. 11A and 11B are views of example containment devices for controlling cold slurry and/or its cooling effect from outside the patient's body.

FIG. 11A shows the cold slurry delivery device 100 of FIG. 1 delivering a cold slurry to the target tissue 105 underneath the patient's skin (which is shown in phantom line). A containment device 600 is applied over the patient's skin to control the spread of the cold slurry and/or its cooling effect from outside the patient's body. The containment device 600 has an opening 605 that defines a containment zone 610 within which the cold slurry and/or its cooling effect is substantially confined. The opening 605 is surrounded by a pressure surface 615 for applying pressure around the containment zone 610. As shown, the containment device 600 is applied with the opening 605 placed over the target tissue 105 and the pressure surface 615 over the surrounding tissue 135 (which is shown in phantom line).

In a convenient example of the containment device 600, the pressure surface 615 is a hollow inside and can expand when filled a fluid or gas, such as air. Force is exerted by pumping air/fluid into the pressure surface 615 causing it to expand and press against the patient's skin. The target tissue 105 experiences little or no pressure because of the opening 605. The surrounding tissue 135, on the other hand, experiences positive pressure. This positive pressure limits the spread of cold slurry and/or its cooling effect from the target tissue 105 to the surrounding tissue 135. Additionally, the pressure exerted can constrict blood vessels in the surrounding tissue 135 and limit warm blood from flowing into the treatment area.

The exerted pressure can be reduced or removed by pumping air/fluid out of the pressure surface 615 causing it to deflate. In a convenient example, the pumping of air/fluid into and out of the pressure surface 615 is done automatically. For example, air/fluid is pumped into the pressure surface 615, such that the containment device 600 applies pressure at or near the start of a cold slurry treatment. After a pre-determined amount of time, the air/fluid is pumped out of the pressure surface 615 relieving pressure from the containment device 600 at or near the end of the cold slurry treatment.

Figure 11B:
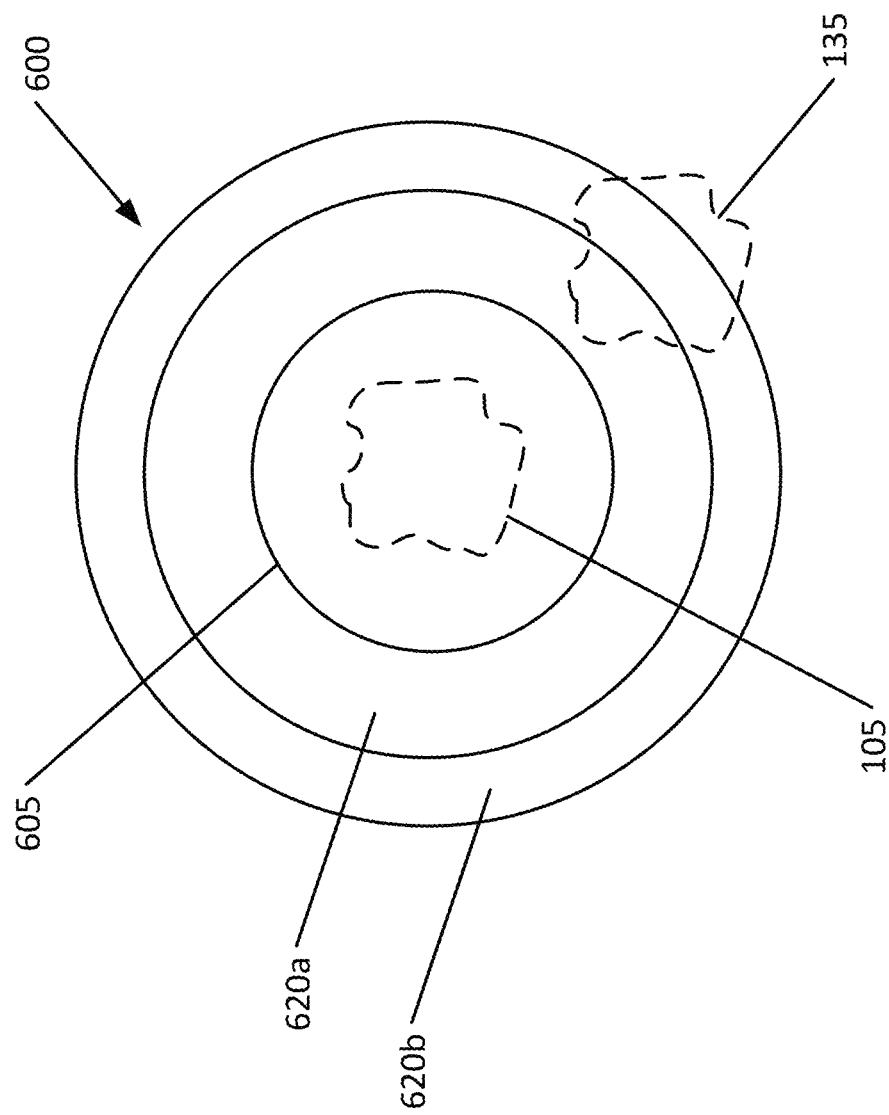

Shown in FIG. 11B, the pressure surface can be divided into segments 620 (shown as a first segment 620a and a second segment 620b). The segments 620 can be, for example, concentric rings. The segments 620 can be filled, individually, such that the pressure exerted pressure by each segment is different. For example, the first segment 620a closest to the opening 605 is filled so that the pressure exerted against the patient's skin is greater that the pressure exerted by the second segment 620b. The difference in pressure applied by the containment device 600 can help control the migration of cold slurry. Additional, the different pressures can facilitate tissue contouring.

In another example of the containment device, the pressure surface is solid. When a force is exerted against the containment device, the target tissue experiences little or no pressure because of the opening. The surrounding tissue, on the other hand, experiences positive pressure. This positive pressure limits the spread of cold slurry and/or its cooling effect from the target tissue to the surrounding tissue. Additionally, the pressure exerted can constrict blood vessels in the surrounding tissue and limit warm blood from flowing into the treatment area.

The solid pressure surface can be divided into segments, for example, concentric rings. The segments can be added or removed to make the size of the opening and, in turn, the containment zone bigger or smaller. The segments can also be added or removed to make the size of the pressure surface bigger or smaller and thus change the area over which pressure is applied.

In the examples shown, the containment device 600 has a circular shape with the opening 605 centrally located and the pressure surface 615 concentric with the opening 605. Further, the pressure surface 615 is a substantially planer surface, as shown. The containment device 600 can be of any shape suitable for applying pressure to a part of the patient's body. For example, the containment device 600 can be rectangular, triangular or other regular shape. The containment device 600 can also have an irregular shape that is adapted to conform to a part of the patient's body being treated. For the example, the containment device 600 can be concaved to saddle, for example, the patient's stomach. The concavity of the containment device 600 is defined in the context of the device in use.

As shown, the opening 605 and pressure surface 615 are axially aligned, i.e., sharing a common axis. In other examples, the axis of the opening 605 and axis of the pressure surface 615 are offset a distance. This non-axial example of the containment device 600 can be useful in applications where it is desirable to bias the containment of cold slurry more or less to one side of the target tissue 105.

The containment device 600 can be made out plastic, polymer, rubber or other material suitable for applying pressure to a part of the patient's body. The containment device can be used manually, for example, a clinician presses (e.g., by way of a handle on the containment device) the device 600 against the patient's skin. Use of the containment device 600 can also be facilitated with straps or clamps for wrapping the containment device 600 around a part of the patient's body.

Figure 12A:
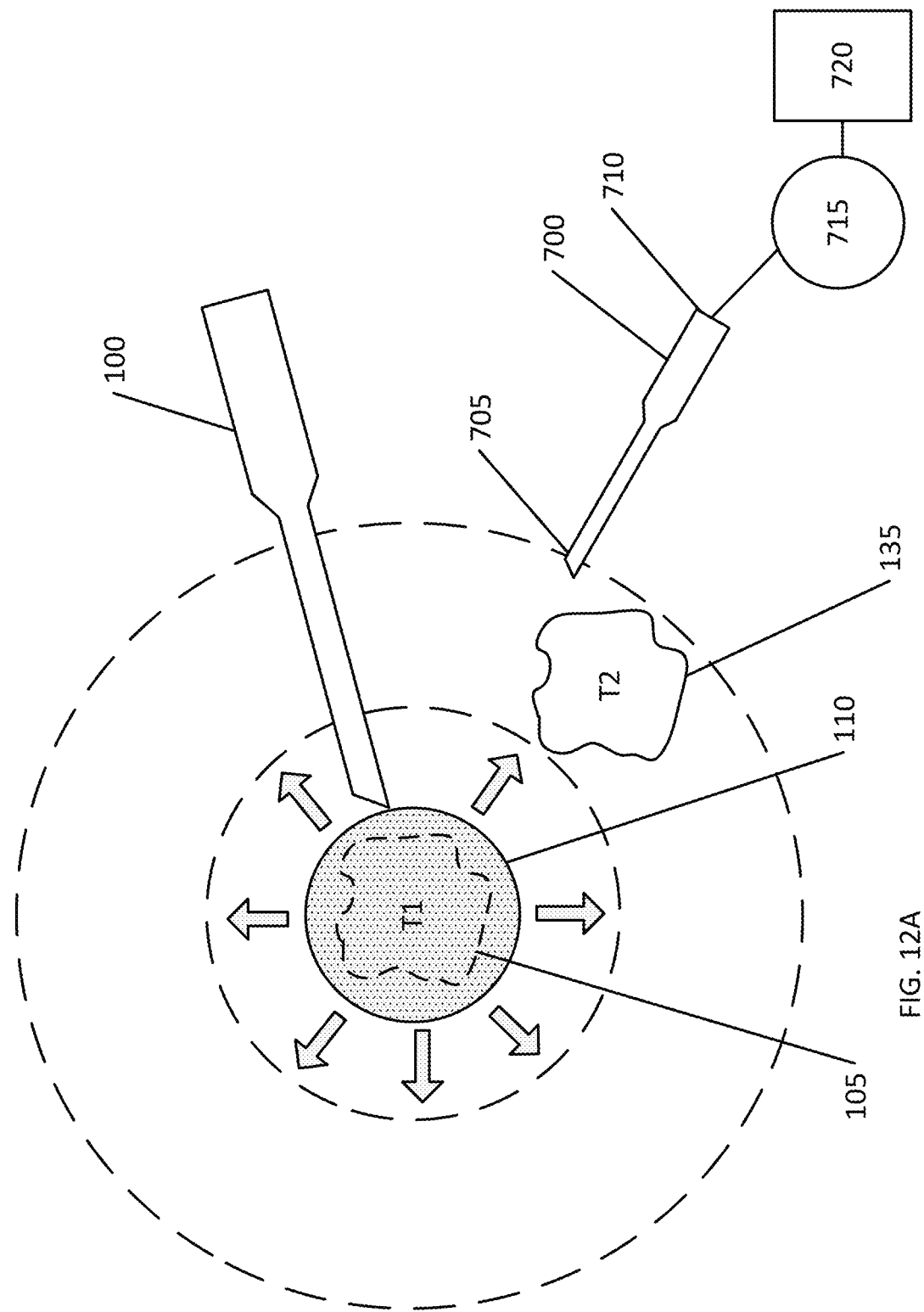
FIGS. 12A and 12B are views of example warm fluid removal devices for removing melted cold slurry from a treatment area.

FIG. 12A shows the cold slurry delivery device 100 of FIG. 1 delivering a cold slurry to the target tissue 105 underneath the patient's skin. Heat from the target tissue 105 is transferred to the cold slurry 110, which in turn lowers the temperature of the target tissue 105 to a first temperature T1. After delivery, the cold slurry 110 spreads out and affects an area larger than the initial delivery site (shown in the figure as arrows radiating outwardly from the delivered cold slurry 110 and dashed circles of increasing size). As the cold slurry 110 spreads out, it melts and lowers the temperature of the surrounding tissue 135 to a second temperature T2, which is warmer than the first temperature T1.

A warm fluid removal device 700 removes the resulting warm fluid from the treatment area. The warm fluid removal device 700 has a distal end 705 that is positioned a distance away for the target tissue 105 and within the surrounding tissue 135. The warm fluid removal device 700 further includes a proximal end 710 that is coupled to a vacuum pump 715. The vacuum pump 715 provides the suction to remove the warm fluid from the treatment area.

The vacuum pump 715 is operatively coupled to a controller 720 for operating the vacuum pump 715. The controller 720 can operate the vacuum pump 715 continuously such that warm fluid is constantly removed. The controller 720 can operate the vacuum pump 715 intermittently such that warm fluid is drawn off at pre-determined intervals. In a convenient example, the controller 720 monitors the temperature of the target tissue 105 using a temperature probe (e.g., one similar to the cold slurry temperature monitor 500 described above with reference to FIGS. 9 and 10). When the temperature of the target tissue 105 rises above the first temperature T1, the controller 720 responds by operating the vacuum pump 715 and removing the warm fluid from the treatment area.

Figure 12B:
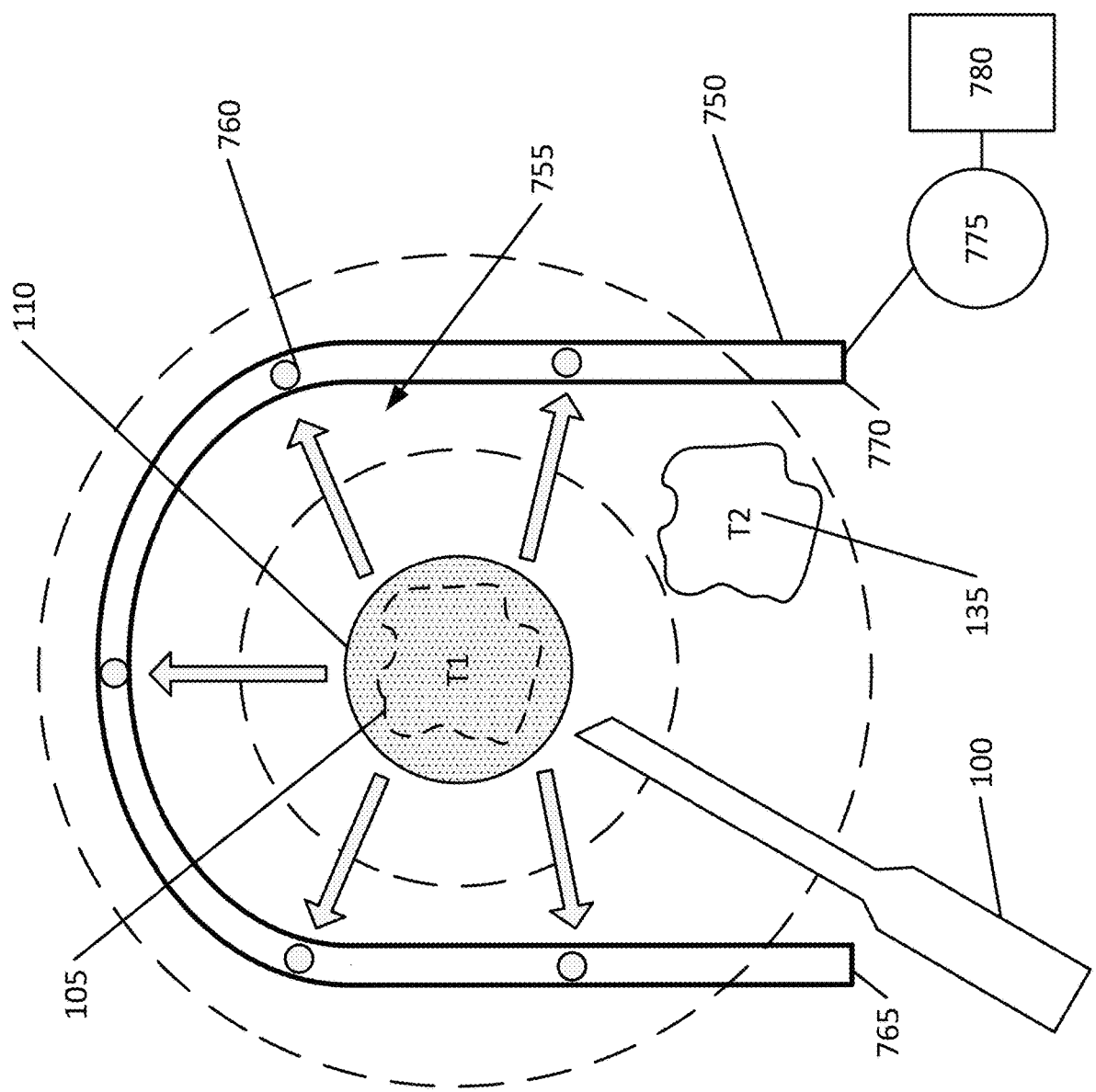

FIG. 12B shows another example warm fluid removal device 750 for removing warm fluid from a treatment area. Generally, the warm fluid removal device 750 has a hoop-like shape. As shown, the warm fluid removal device 750 is U-shaped with an open end 755 facing the target tissue 105. The warm fluid removal device 750 further has a plurality of holes 760 defined along its length through which warm fluid is removed from the treatment area (shown as arrows). The warm fluid removal device 750 can include an open distal end 765 to further enhance removal of the warm fluid from the treatment area. In a convenient example, the warm fluid removal device 750 has a non-operating mode and an operating mode. In the non-operating mode, the warm fluid removal device 750 is substantial linear in shape. In the non-operating mode, the warm fluid removal device 750 can be readily inserted through the patient's skin, advanced to the tissue surrounding the target tissue, and removed from the patient.

In the operating mode, the warm fluid removal device 750 is U-shaped with the open end 755 facing the target tissue 105 as shown in FIG. 12B. The warm fluid removal device 700 can be mechanically actuated between the non-operating mode and operating mode with a tension wire, for example. In another example, the warm fluid removal device 750 is made for a shape memory alloy, such as nitinol.

The warm fluid removal device 750 further includes a proximal end 770 that is coupled to a vacuum pump 775. The vacuum pump 775 provides the suction to remove the warm fluid of the treatment area. The controller 781 can operate the vacuum pump 775 continuously such that warm fluid is constantly removed. The controller 720 can operate the vacuum pump 775 intermittently such that warm fluid is drawn off at pre-determined intervals. In a convenient example, the controller 780 monitors the temperature of the target tissue 105 using a temperature probe (e.g., one similar to the cold slurry temperature monitor 500 described above with reference to FIGS. 9 and 10). When the temperature of the target tissue 105 rises above the first temperature T1, the controller 780 operates the vacuum pump 775 to remove the warm fluid from the treatment area.

The warm fluid removal device 700 of FIG. 12A (or 650 of FIG. 12B) and the cold slurry delivery device 100 of FIG. 1 can be operated together, for example, using the controller 720, to replenish "old" cold slurry with "fresh" cold slurry. Replenishing cold slurry can occur intermittently such that warm fluid is drawn off and cold slurry is delivered at pre-determined intervals.

In a convenient example, the controller 720 monitors the temperature of the target tissue 105 using a temperature probe (e.g., one similar to the cold slurry temperature monitor 500 described above with reference to FIGS. 9 and 10). When the temperature of the target tissue 105 rises above the first temperature T1, the controller 720 responds by operating the warm fluid removal device 700 to remove warm fluid from the treatment area; and by operating the cold slurry delivery device 105 to deliver cold slurry to the target tissue 105. This configuration is particular useful for cooling tissue for an extended period of time.

In a convenient example, any one of the devices described above can be deployed using a guide. FIGS. 13A-13C show an example of the guide 800 to use with the deployment device 115 of FIG. 1. The guide 800 includes a working channel 805 for housing the application cannula 120 and the balloon 130. The working channel 800 is inserted through the patient's skin and advanced towards the treatment area. At the treatment area, the deployment device 115 is pushed out of the working channel, as shown in FIG. 13B. The balloon 130 is then be inflated with a fluid or a gas, such as air, as shown in FIG. 13C, and used to control the cold slurry and/or its cooling effects, as described above. When the treatment is done, the balloon 130 is deflated and pulled back into the working channel 805. The guide 800 is then withdrawn from the patient's body. The guide 800 can have one or more working channels to control the function of the balloon or a collection of balloons.

Figure 14A:
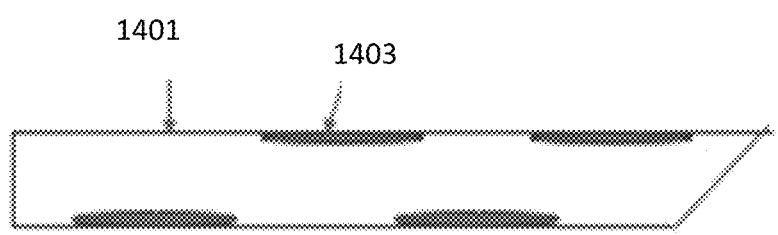
FIGS. 14A and 14B show a fenestrated cannula with balloons in retracted and expanded states.
Figure 14B:
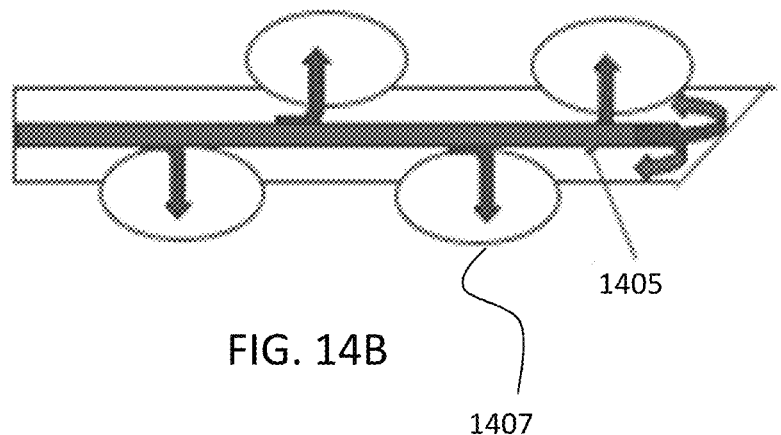

In various embodiments, fenestrated needles or cannulas are provided with one or more mini or micro balloons that, when filled with a therapeutic cold fluid or slurry, drastically increase surface area through which the cannula can transfer heat from surrounding tissue. The balloons may be modeled after intestinal villi for example and may be deployed from a single needle or cannula as shown in FIGS. 14A and 14B or through an array of needles or cannulas. The expansion and retraction of the balloons can be dependent on a differential in wall pressure when slurry or cold solution flows through the cannula or needle.

An exemplary fenestrated needle or cannula is shown in FIGS. 14A and 14B. The fenestrated cannula 1401 may be constructed of a relatively rigid or inflexible material compared to the balloon 1407 material. Balloons 1407 formed of a relatively flexible or expansible material are present in a series of openings 1403 in the rigid cannula 1401. The cannula 1401 may have a solid tip to allow pressure to build within a lumen 1405 of the cannula as slurry or fluid is added. As fluid or slurry is added and pressure within the lumen 1405 builds, the relatively flexible balloons 1407 expand outwardly through the openings 1403 as shown in FIG. 14B. The resulting expanded balloons, filled with cold slurry, drastically increase the surface area for thermal interaction with surrounding tissue. Once fluid or slurry flow ceases, the expanded balloons 1407 retract back within the openings 1403 as shown in FIG. 14A, allowing for ease of insertion and removal of the cannula.

Figure 15:
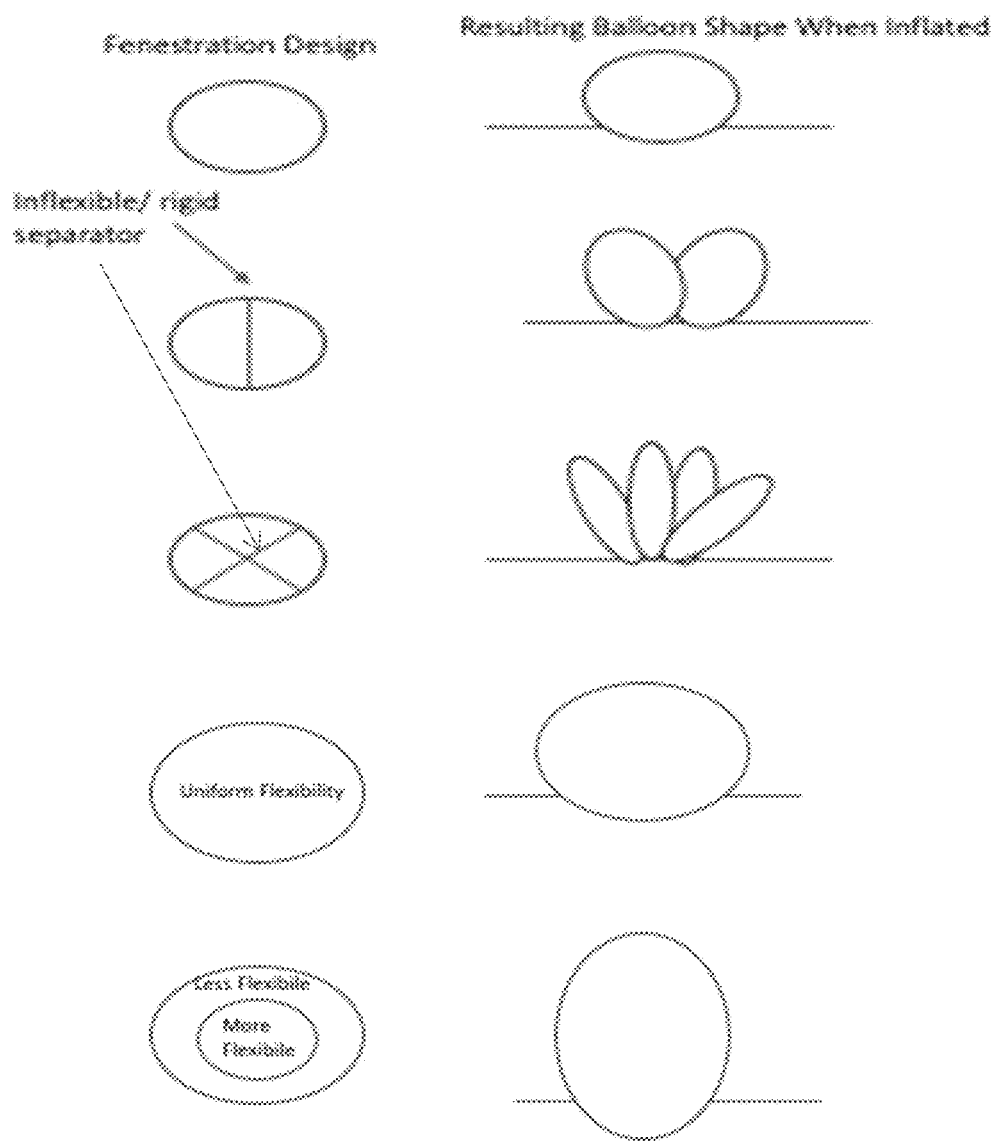
FIG. 15 shows various opening designs for a fenestrated cannula and the resulting shapes of balloons expanded therethrough with slurry.

The micro or mini balloons of fenestrated cannulas may be a variety of different shapes as shown in FIG. 15. The left column of FIG. 15 illustrates the shape of various openings in fenestrated cannula embodiments of the invention and the right column shows a corresponding balloon shape one a balloon is expanded through an opening of the shape shown in the left column. For example, a rigid material such as that of the cannula itself may be used to divide the opening as shown in FIG. 15. By dividing the opening in two or in quarters, a balloon expanding therethrough will form two or four separate expanded members. In certain embodiments, the flexibility of the balloon material within an opening may be varied as shown in FIG. 15 to cause the expanded balloon to take on different shapes. For example, concentric rings of varying flexibility may result in an oblong expanded balloon which may be advantageous for certain treatments.

What is claimed is:

1. A device for controlling tissue temperature, the device comprising:
   a first cannula for delivering a cold slurry directly to a target tissue underneath a patient's skin, thereby directly contacting and cooling the target tissue, the first cannula comprising a first open distal end and a first proximal end in fluid communication with a source of cold slurry;
   a second cannula comprising a second open distal end and a second proximal end in fluid communication with a source of a thermal insulator; and
   a balloon disposed around the second open distal end of the second cannula and positioned at or near tissue surrounding the target tissue, the balloon comprising a volume filled with the thermal insulator delivered through the second cannula, wherein the filled balloon limits heat from transferring from the surrounding tissue to the target tissue.

2. The device of claim 1, wherein the first and second cannulas each have a size and shape suitable for inserting through a subject's skin.

3. The device of claim 1 further comprising a cold slurry temperature monitor extending beyond the first open distal end to measure a temperature of the delivered cold slurry.

4. The device of claim 3, wherein the cold slurry temperature monitor includes a temperature sensor at a distal end of the cold slurry temperature monitor.

5. The device of claim 4, wherein the temperature sensor is a forward infrared (FIR) sensor.

6. The device of claim 3, wherein the cold slurry temperature monitor includes a plurality of temperature sensors spaced along a length of the cold slurry temperature monitor.

7. The device of claim 1, wherein the thermal insulator is any one of fluid, gas, air, gel, and aerogel.

8. The device of claim 1, wherein the cold slurry is a mixture of water and glycerol.

9. The device of claim 1, wherein the balloon has a length that is greater than its width.

10. The device of claim 1, wherein the balloon is generally spherical.

11. The device of claim 1, wherein the balloon has a longitudinal axis and is concaved as defined by a point along a line parallel to and offset from the longitudinal axis.

12. The device of claim 1 further comprising a guide, the guide comprising a working channel sized to house the second cannula and the balloon disposed around the second cannula; and wherein the balloon is deployed from the working channel when in use.

13. The device of claim 1, wherein the balloon has a linear shape.

14. The device of claim 1, wherein the balloon has a ring shape.

15. The device of claim 1, wherein the second cannula is configured to be insertable through the patient's skin.

16. The device of claim 1, wherein the balloon has a plurality of projecting arms.

17. The device of claim 1, wherein the balloon has a plurality of chambers which can be opened or closed to control the shape of the balloon.

18. The device of claim 1, wherein the balloon has a plurality of chambers, each of which is filled with a gas or a fluid.

19. The device of claim 18, wherein the temperatures of the gas or the fluid in each of the plurality of chambers of the balloon are different.

* * * * *